US012616415B2

(12) United States Patent (10) Patent No.: US 12,616,415 B2
Lerman et al. (45) Date of Patent: May 5, 2026

(54) NEURAL SIGNAL DETECTION OF IMMUNE RESPONSES

(71) Applicant: THE REGENTS OF THE UNIVERSITY OF CALIFORNIA, Oakland, CA (US)

(72) Inventors: Imanuel Lerman, San Diego, CA (US); Ramesh Rao, La Jolla, CA (US); Ming-Xiong Huang, La Jolla, CA (US); Todd P. Coleman, La Jolla, CA (US); Yifeng Bu, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 3 days.

(21) Appl. No.: 18/292,659

(22) PCT Filed: Jul. 25, 2022

(86) PCT No.: PCT/US2022/038219
§ 371 (c)(1),
(2) Date: Jan. 26, 2024

(87) PCT Pub. No.: WO2023/009453
PCT Pub. Date: Feb. 2, 2023

(65) Prior Publication Data
US 2025/0082258 A1     Mar. 13, 2025

Related U.S. Application Data

(60) Provisional application No. 63/226,087, filed on Jul. 27, 2021.

(51) Int. Cl.
*A61B 5/00*     (2006.01)
*A61B 5/248*     (2021.01)
(Continued)

(52) U.S. Cl.
CPC ................ *A61B 5/41* (2013.01); *A61B 5/248* (2021.01); *A61B 5/388* (2021.01); *A61B 5/6833* (2013.01);
(Continued)

(58) Field of Classification Search
CPC ....... A61B 5/388; A61B 5/294; A61B 5/4035; A61B 5/41; A61B 5/414; A61B 5/0022;
(Continued)

(56) References Cited

U.S. PATENT DOCUMENTS 6,907,280 B2 *   6/2005   Becerra ................ A61B 5/4824
                                                    600/407
7,562,981 B2 *   7/2009   Togino ................... A61B 3/113
                                                    351/223
(Continued)

FOREIGN PATENT DOCUMENTS

WO       2018195238 A1     10/2018
WO       2019/143790 A1     7/2019

OTHER PUBLICATIONS

ISA, International Search Report and Written Opinion for International Application No. PCT/US2022/038219, mailed on Nov. 29, 2022, 9 pages.
(Continued)

*Primary Examiner* — Oommen Jacob
(74) *Attorney, Agent, or Firm* — Perkins Coie LLP

(57)     ABSTRACT

Disclosed are devices, systems and methods for neural signal detection of immune responses. In some aspects, a system includes a processing unit: a receiving unit configured to receive at least one sensor signal from a wearable sensor, where the wearable sensor is configured to detect at least one neural signal of a patient; and a tangible non-transitory computer readable medium having instructions configured to cause the processing unit to automatically
(Continued)

receive a data signal from the receiving unit, automatically detect an immune response based at least in part on the data signal, automatically create a notification based at least in part on the immune response, and automatically present the notification to a user of the system.

21 Claims, 18 Drawing Sheets

(51) Int. Cl.
  A61B 5/388 (2021.01)
  G16H 10/60 (2018.01)
(52) U.S. Cl.
  CPC ...... *A61B 2562/0223* (2013.01); *G16H 10/60* (2018.01)
(58) Field of Classification Search
  CPC ..... A61B 5/7246; A61B 5/7282; A61B 5/746; G16H 10/60
  See application file for complete search history.

(56) References Cited

U.S. PATENT DOCUMENTS

| | | | | |
|---|---|---|---|---|
| 9,849,241 | B2* | 12/2017 | Becker | G16H 20/17 |
| 2007/0010723 | A1* | 1/2007 | Uutela | A61B 5/33 |
| | | | | 128/920 |
| 2009/0325167 | A1* | 12/2009 | Chappell | G01N 33/564 |
| | | | | 435/7.1 |
| 2013/0245486 | A1* | 9/2013 | Simon | A61B 5/4836 |
| | | | | 607/46 |
| 2014/0288620 | A1 | 9/2014 | DiLorenzo | |
| 2015/0335288 | A1 | 11/2015 | Toth et al. | |
| 2016/0157772 | A1* | 6/2016 | Grant | A61B 5/486 |
| | | | | 600/407 |
| 2016/0250097 | A9 | 9/2016 | Tracey et al. | |
| 2017/0007853 | A1 | 1/2017 | Alford et al. | |
| 2017/0231490 | A1* | 8/2017 | Toth | G16H 40/63 |
| | | | | 600/558 |
| 2018/0117320 | A1 | 5/2018 | Levine et al. | |
| 2019/0167211 | A1* | 6/2019 | Everman | G09B 9/10 |
| 2019/0321640 | A1 | 10/2019 | Carmena et al. | |
| 2020/0179600 | A1 | 6/2020 | Zanos et al. | |
| 2020/0196932 | A1* | 6/2020 | Johnson | A61B 5/7455 |
| 2020/0346043 | A1 | 11/2020 | Puleo et al. | |
| 2021/0401314 | A1* | 12/2021 | Pho | A61B 5/6826 |
| 2022/0276224 | A1* | 9/2022 | Rao | G16H 20/10 |
| 2025/0082258 | A1* | 3/2025 | Lerman | A61B 5/414 |

OTHER PUBLICATIONS

EPO Extended European Search Report mailed Apr. 17, 2025 for European Application No. 22850146.6, Applicant: The Regents of the University of California, 12 pages.

* cited by examiner

NEURAL SIGNAL DETECTION OF IMMUNE RESPONSES

CROSS-REFERENCE TO RELATED APPLICATIONS

This patent document claims priorities and benefits of U.S. Provisional Application No. 63/226,087, titled "NEURAL SIGNAL DETECTION OF IMMUNE RESPONSES" and filed on Jul. 27, 2021. The entire content of the afore-mentioned patent application is incorporated by reference as part of the disclosure of this patent document.

TECHNICAL FIELD

This patent document relates to wearable sensor technology.

BACKGROUND

Many conventional methods for determining disease states employ blood cultures and/or laboratory tests. Yet, conventional methods are time typically time-consuming causing delays in disease state identification in patients, which may delay treatment.

Some conventional systems and technological processes may generate neuromodulation signals to stimulate periph-eral nerves in a patient. Some of these systems may detect a response to nerve stimulation. Some of these conventional systems and technological processes may determine a dis-ease in a patient that is neurologic and/or psychiatric, based on the response to the nerve stimulation.

Other conventional systems and technological processes may measure nerve activities in a patient through employ-ment of invasively-implanted electrodes in patients with diabetes.

Therefore, a need exists for more efficient and noninva-sive early stage detection of disease states.

SUMMARY

Disclosed are devices, systems and methods for neural signal detection of immune responses. Immune and inflam-matory responses are controlled by the vagus nerve in response to pathogen invasion, tissue injury, and other stimuli. Thus, certain vagus nerve signal features/signatures are correlated with immune responses to different stimuli. According to various embodiments described herein, a cata-log of vagus nerve signal signatures is generated. Vagus nerve activity and other physiological signals of a given subject are monitored and compared against the features/signatures of the catalog. Based on this comparison, early detection of pathogen exposure of the given subject can be accomplished. Further, early detection of immune responses, such as cytokine release, can enable early detec-tion of sepsis and septic shock caused by dysregulated or excessive cytokine concentrations.

In one exemplary aspect, a system for pre-symptomatic detection of pathogen-stimulated immune responses via neural signals is disclosed. The system includes a processing unit including a processor configured to cause the system to, for a first subject stimulated with a known pathogen, obtain-ing a neural signal and a physiological signal from a cervical region of the first subject through which a vagus nerve of the first subject extends. The neural signal includes a vagus nerve signal that is autonomically communicated through the vagus nerve as an immune response to the known pathogen. The processor is configured to further cause the system to extract, from the neural signal and the physiologi-cal signal, a plurality of historical labels that correlate signal features across the neural signal and the physiological signal with the known pathogen. The processor is configured to further cause the system to for a second subject, monitor a second neural signal of the second subject via a wearable device adhered to a cervical region of the second subject through which a vagus nerve of the second subject extends. The processor is configured to further cause the system to, based on identifying a particular signal feature in the second neural signal that is correlated with the known pathogen according to the plurality of historical labels, determine an occurrence of the immune response to the known pathogen in the second subject. The processor is configured to further cause the system to cause a notification of the occurrence of the immune response to the known pathogen to be presented to the second subject via a personal device associated with the second subject.

In another exemplary aspect, a method for early detection of immune response of a subject is disclosed. The method includes receiving, via a wearable sensor attached to a surface of the subject, at least one neural signal of the subject and at least one physiological signal of the subject detected by the wearable sensor. The method further includes com-paring a plurality of signal features across the at least one neural signal and the at least one physiological signal with historical signal labels associated with one or more past immune responses. The method further includes identifying an occurrence of an immune response of the subject based on the comparing. The method further includes causing a notification of the occurrence of the immune response to be presented to the subject via a personal device for the subject.

In another exemplary aspect, a non-transitory computer readable medium having executable computer code stored thereon is disclosed. The executable computer code includes instructions configured to cause a processor to perform operations including receiving, via a wearable sensor attached to a surface of the subject, at least one neural signal of the subject and at least one physiological signal of the subject detected by the wearable sensor; comparing a plu-rality of signal features across the at least one neural signal and the at least one physiological signal with historical signal labels associated with one or more past immune responses; based on the comparing, identifying an occur-rence of an immune response of the subject; and causing a notification of the occurrence of the immune response to be presented to the subject via a personal device for the subject.

In another exemplary aspect, a system for immune response identification is disclosed. The system includes a wearable device attached to a surface of a subject. The wearable device is configured to transcutaneously collect sensor data from the subject. The system further includes a processing unit that includes at least one processor and at least one memory. The at least one processor executes instructions stored on the at least one memory to cause the processing unit to detect, via data received from the wear-able sensor, at least one neural signal of the subject and at least one physiological signal of the subject. The at least one processor further causes the processing unit to compare a plurality of signal features across the at least one neural signal and the at least one physiological signal with histori-cal signal labels associated with historical immune responses. The at least one processor further causes the processing unit to identify an occurrence of an immune response of the subject based on the comparing. The at least one processor further causes the processing unit to cause a notification of the occurrence of the immune response to be presented to the subject via a personal device for the subject.

In some aspects, a system includes a processing unit; a receiving unit configured to receive at least one sensor signal from a wearable sensor, where the wearable sensor is configured to detect at least one neural signal of a patient; and a tangible non-transitory computer readable medium having instructions configured to cause the processing unit to automatically receive a data signal from the receiving unit, automatically detect an immune response based at least in part on the data signal, automatically create a notification based at least in part on the immune response, and automatically present the notification to a user of the system.

The subject matter described in this patent disclosure can be implemented in specific ways that provide one or more of the following features.

4

Figure 17:
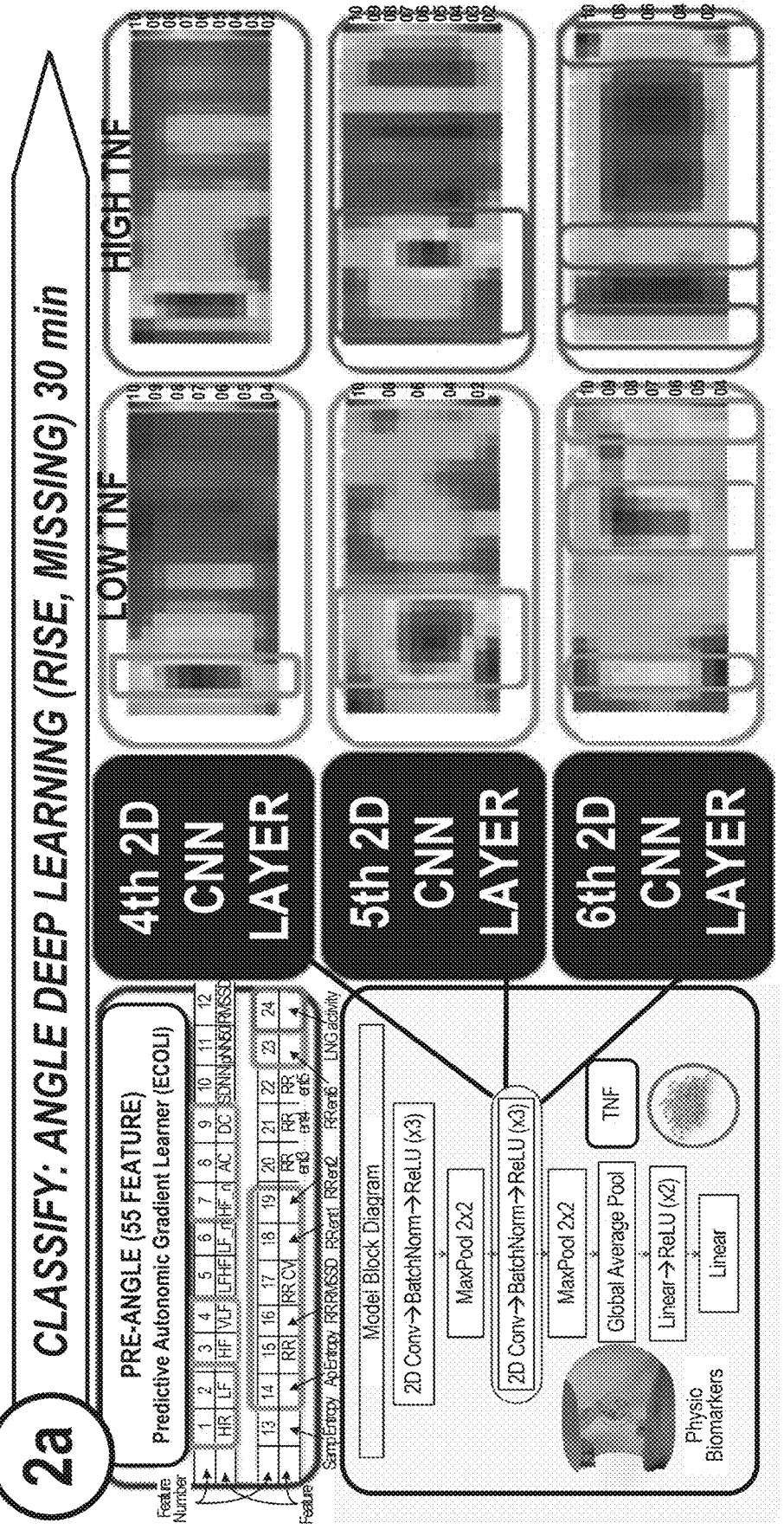

FIG. 17 shows a diagram illustrating an example embodiment of a convolutional neural network (CNN) for an exemplary machine learning or deep learning model(s) in accordance with the present technology.

Figure 18:
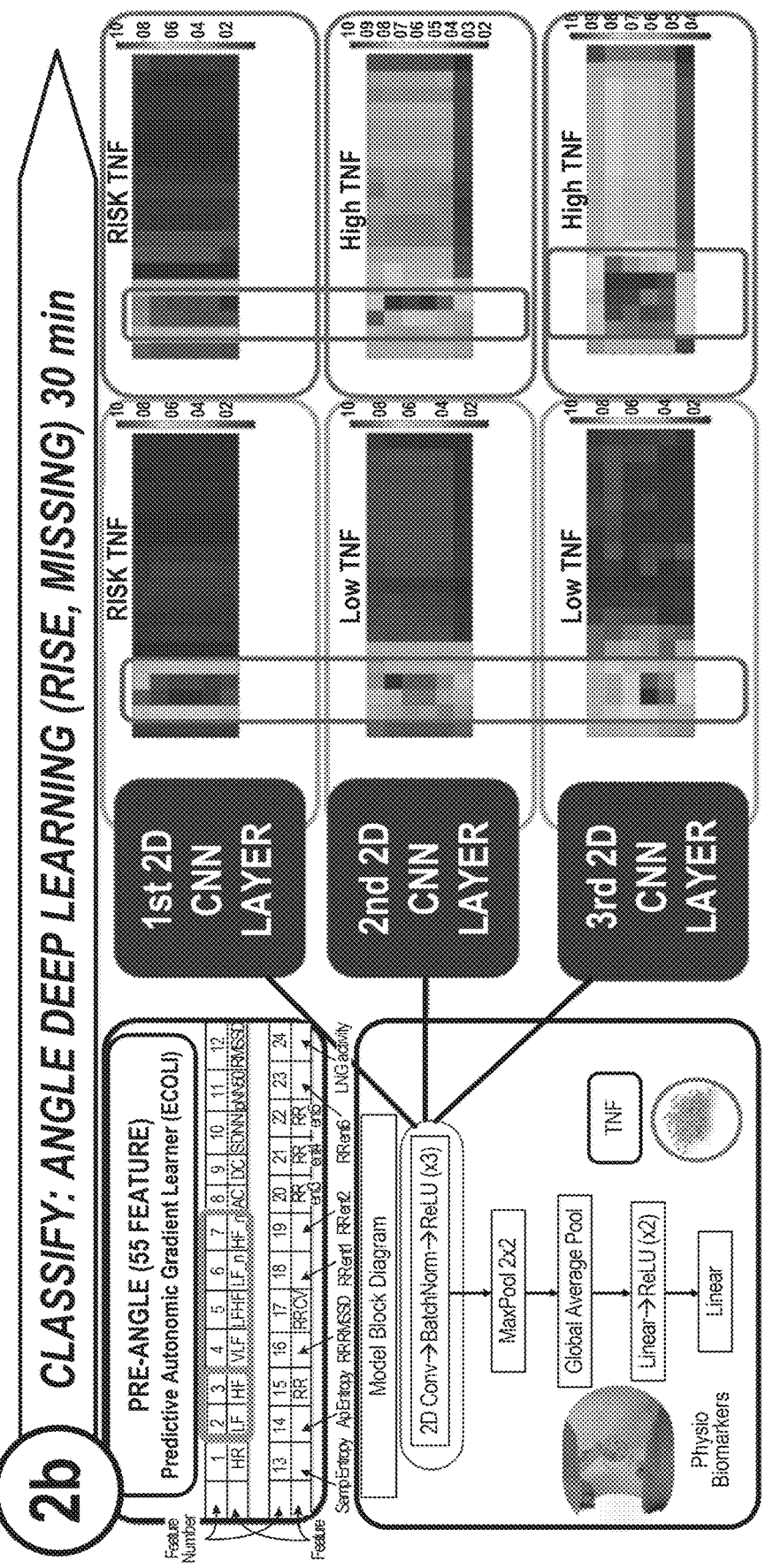

FIG. 18 shows a diagram illustrating an example embodiment of a convolutional neural network (CNN) for an exemplary machine learning or deep learning model(s) in accordance with the present technology.

DETAILED DESCRIPTION

Disclosed are devices, systems, and methods for neural signal detection of immune responses. Embodiments consistent with the present disclosure are rooted in computer and sensor technologies and may include collecting, storing, and/or processing various types of signals including neural signals. Collecting and processing neural signals according to the disclosed embodiments can improve effectiveness of identifying root-cause(s) of immune response(s) in patients. A root-cause of an immune response can be a specific pathogen. Collecting and processing neural signals according to the disclosed embodiments may lead to improved efficiency in treating root-cause(s) of immune response(s) in patients. Immune response(s) and/or root-cause(s) of immune response(s) may be identified in pre-symptomatic patients through employment of the embodiments in accordance with the disclosed technology. The disclosed systems and methods can improve efficiency in detecting early stage inflammation and/or cytokine response(s) in a patient over conventional devices and technological processes. Collecting and processing neural signals using the disclosed system and methods, prior to any infection (e.g., during pre-infectious regular activity), can predict host immune response severity, morbidity, and mortality in patients through employment of the disclosed embodiments.

In some aspects, systems and methods are disclosed for detecting a change in an immune response. Changes in immune responses may indicate inflammation progression; patient improvement, where, for example, patient improvement may be based on medical treatment; and/or patient deterioration.

In some aspects, systems and methods are disclosed for detecting pre-infection or pre-inflammation activity based on baseline recording that may predict a change in inflammation associated with an infection.

Figure 1:
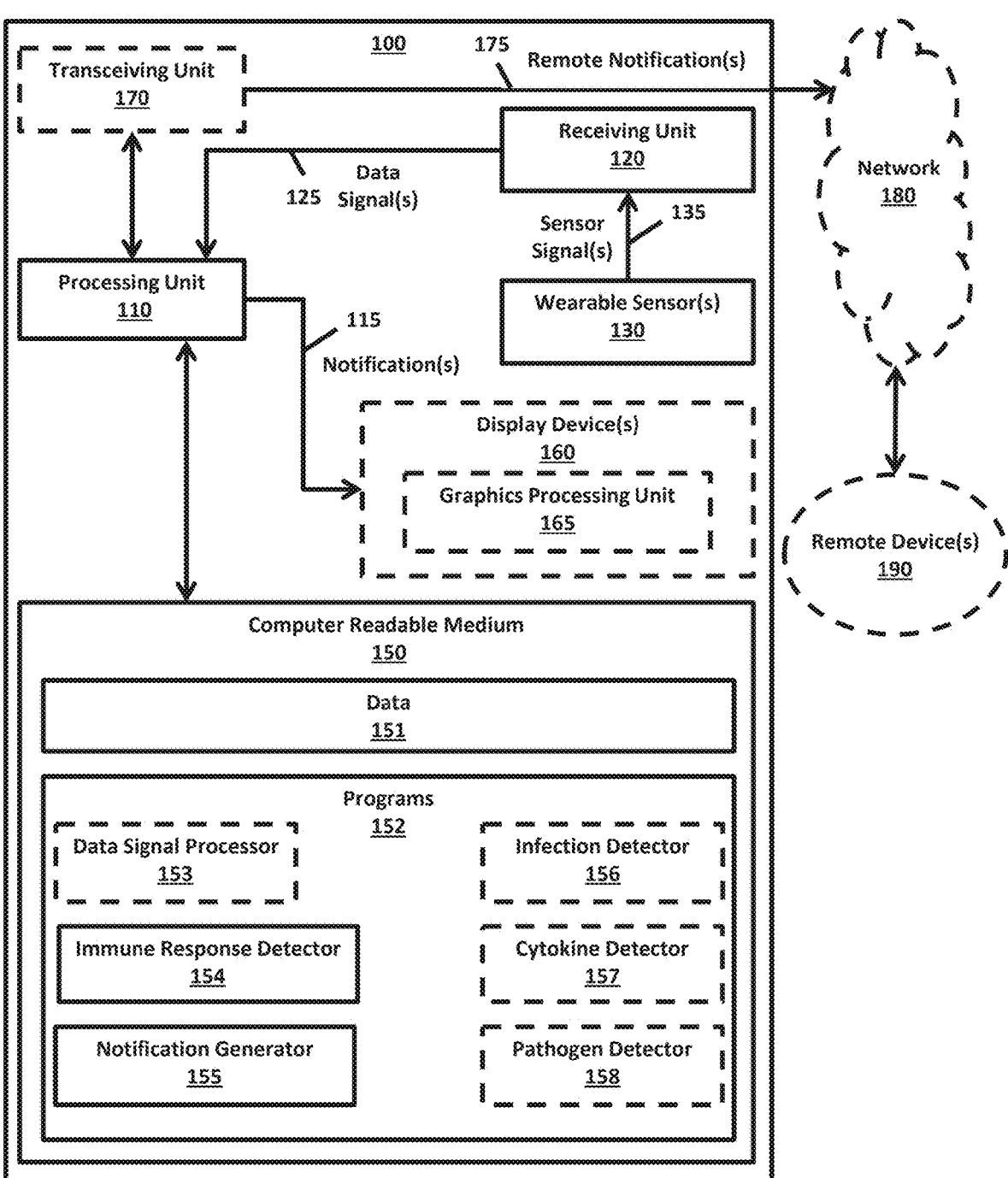
FIG. 1 is a block diagram of an example embodiment of a system for neural signal detection of immune responses in accordance with the disclosed technology.

FIG. 1 is a block diagram of a system 100 for neural signal detection of immune responses, consistent with disclosed embodiments. System 100 can include a processing unit 110, a receiving unit 120, a wearable sensor 130, and a tangible non-transitory computer readable medium 150. The processing unit 110 can include at least one processor. The receiving unit 120 can include at least one receiver. The receiving unit 120 can be configured to receive sensor signal/signals 135. Sensor signal/signals 135 can be communicated from the wearable sensor 130. Sensor signal 135 can include a plurality of sensor signals communicated from a plurality of wearable sensors 130. Wearable sensor 130 can be configured to detect at least one neural signal(s) of a patient. Wearable sensor 130 can be configured to detect at least one neural signal transcutaneously. At least one of the sensor signals 135 can include at least a portion of a neural signal. The receiving unit 120 can be configured to communicate data signal(s) 125 to the processing unit 110. Data signal(s) 125 can include a plurality of data signals. The computer readable medium 150 can include data 151 and programs 152. Data 151 may have data corresponding to the sensor signals 135, the data signals 125, physiological signals, and/or any other data corresponding to a patient. Programs 152 can include instructions. The processing unit 110 can be configured to execute instructions stored in programs 152. Programs 152 can include an immune response detector 154. Programs 152 can have a notification generator 155. The particular arrangement of components depicted in FIG. 1 is not limiting. The system 100 can include additional components, or fewer components. Multiple components of system 100 can be implemented using the same physical computing device or different physical computing devices.

In some embodiments, for example, a wearable sensor (e.g., 130) can include an electrocardiogram (ECG) sensor, an electroencephalographic (EEG) sensor, and/or a magnetization sensor, e.g., a magnetoencephalography (MEG) sensor. In some embodiments, the wearable sensor includes an array of electrodes that each detect at least a portion of a signal.

In some example embodiments of the computer readable medium 150, the system 100 can include an immune response detector 154. The immune response detector 154 can include instructions configured to cause processing the unit 110 to automatically detect an immune response based at least in part on the data signal/signals 125 analyzed in accordance with a data processing protocol of the immune response detector 154. The immune response detector 154 can include instructions configured to cause the processing unit 110 to automatically detect a change in the immune response. The change in immune response can be automatically detected based on identifying certain signal features or aspects of data signal/signals 125 collected from the subject. For example, when the data signal/signals 125 includes a neural signal, and based on identifying a change in signal features or aspects, such as a number of neural spikes, average signal amplitude, spike frequency, signal duration, or other factor of the neural signal, a change in immune response can be automatically detected by the immune response detector 154.

Some embodiments of the system 100 can include a notification generator 155. The notification generator 155 can include instructions configured to cause the processing unit 110 to automatically create a notification based at least in part on an immune response. The notification generator 155 can include instructions configured to cause processing unit 110 to automatically create a change notification based at least in part on a change in the immune response.

In some embodiments, for example, the programs 152 can include instructions configured to cause the processing unit 110 to automatically present the notification(s) 115 to a user of the system 100. Notification/notifications 115 can include a change notification. By way of example and not limitation, notification(s) 115 can include: an alert, a message, streaming data, and/or any other notifications. Notification(s) 115 can be communicated to a display device 160. The display device 160 can include a plurality of display devices. Display device 160 may be associated with graphics processing unit 165 configured to render notification(s) 115 for presentation on the display device 160.

In some embodiments, for example, the programs 152 can include instructions configured to cause the processing unit 110 to automatically present a plot of at least one data signal 125 on at least one display 160. A plot can include a plurality of spikes in amplitude of one or more neural signals.

In some embodiments, the system 100 can include a transceiving unit 170. The transceiving unit 170 can include at least one transceiver. A transceiver can include at least one transmitter and at least one receiver. A transceiver may be configured to communicate with at least one remote device

190. A transceiver may be configured to communicate with the remote device 190 via, for example, Wi-Fi, Bluetooth, Bluetooth Low Energy (BLE), Zigbee, 3G/4G/LTE/5G cellular communication methods, and/or any other communication protocols. A transceiver can include one or more antennas. The programs 152 can have instructions configured to cause the processing unit 110 to automatically communicate a notification to the remote device 190 employing transceiving unit 170. The notification can include at least one remote notification 175. A remote notification 175 can include a change notification. By way of example and not limitation, at least one remote notification 175 can include: an alert, a message, streaming data, and/or any other notification. A remote device 190 can include a plurality of remote devices. The remote notification 175 may be communicated from the transceiving unit 170 to the remote device 190 through the employment of network 180. By way of example and not limitation, remote device 190 can be employed by: a user, a remote operator, a medical professional, and/or any other user. The system 100 may be configured to accept operational instructions from the remote device 190.

In some embodiments, the programs 152 can include instructions configured to cause the processing unit 110 to automatically communicate data signal(s) 125 to at least one remote device 190 through the employment of transceiving unit 170.

In some embodiments, the programs 152 can include instructions configured to cause the processing unit 110 to automatically receive data signal/signals 125 from a receiving unit 120. The data signal/signals 125 can include one or more sensor signals 135. The receiving unit 120 can include an amplifier. The receiving unit 120 can be configured to apply one or more filters to one or more sensor signals 135. The receiving unit 120 can be configured to convert analog sensor signals into digital sensor signals. The programs 152 can include a data signal processor 153. The data signal processor 153 can include instructions configured to cause the processing unit 110 to automatically process data signal(s) 125. Processing data signal(s) 125 can include filtering, modulating, encoding, converting analog signals to digital, converting digital signals to analog, performing error correction, and/or multiplexing a plurality of signals. Data signal(s) 125 may be processed prior to communication to at least one remote device 190. In some embodiments, the data signal/signals 125 represent neural signals (e.g., vagus nerve signals) or physiological signals.

In some example embodiments the computer readable medium 150, the system 100 can include an infection detector 156. The infection detector 156 can include instructions configured to cause the processing unit 110 to automatically determine that an immune response is based on an infection in a patient. A determination that an immune response is based on an infection in a patient may be based on the detection of at least one neural signal of the patient. Alternatively, or additionally, a determination that an immune response is based on an infection in a patient may be based on a heart rate, a respiratory rate, a respiratory phase, and/or electrodermal activity of the patient. For example, at least one neural signal may be detected and/or analyzed at peak inspiration of a respiratory cycle in a patient. Thus, in some embodiments, the neural signal is correlated with a physiological signal of the patient in order to identify certain signal features of the neural signal. A determination that an immune response is based on an infection in a patient may be based on processing one or more data signals 125. For example, certain signal features are identified in the at least one neural signal and/or the physiological signals (e.g., the heart rate, the respiratory rate, the respiratory phase, electrodermal activity). The certain signal features across the at least one neural signal and/or the physiological signals are compared against historical labels that are associated with past patient infections. The historical labels may be specific to the patient, specific to a demographic of the patient, and/or the like.

In some embodiments the computer readable medium 150, the system 100 can include a cytokine detector 157. The cytokine detector 157 can include instructions configured to cause the processing unit 110 to automatically determine that an immune response is based on a cytokine response in a patient. A cytokine response can include one or more cytokine types and/or cytokine concentrations. The cytokine detector 157 can include instructions configured to cause processing unit 110 to automatically determine that a cytokine response is based on a specific cytokine, cytokine concentration, and/or cytokine type. A determination that an immune response is based on a cytokine response in a patient may be based on the detection of at least one neural signal of the patient. A determination that an immune response is based on a cytokine response in a patient may be based on a heart rate, a respiratory rate, a respiratory phase, and/or electrodermal activity of the patient. For example, at least one neural signal may be detected and/or analyzed at peak inspiration of a respiratory cycle in a patient. Thus, in some embodiments, the neural signal is correlated with a physiological signal of the patient in order to identify certain signal features of the neural signal. A determination that an immune response is based on a cytokine response in a patient may be based on processing one or more data signals 125. For example, certain signal features are identified in the at least one neural signal and/or the physiological signals (e.g., the heart rate, the respiratory rate, the respiratory phase, electrodermal activity). The certain signal features across the at least one neural signal and/or the physiological signals are compared against historical labels that are associated with past cytokine responses. The historical labels may be specific to the patient, specific to a demographic of the patient, and/or the like.

In some embodiments the computer readable medium 150, the system 100 can include a pathogen detector 158. The pathogen detector 158 can include instructions configured to cause the processing unit 110 to automatically determine that an immune response is based on a pathogen in a patient. A determination that an immune response is based on a pathogen in a patient can be based on the detection of at least one neural signal of the patient. A determination that an immune response is based on a pathogen in a patient may be based on processing one or more data signals 125. The pathogen detector 158 can include instructions configured to cause the processing unit 110 to automatically identify a specific pathogen in a patient. Identification of a specific pathogen in a patient may be based on the detection of at least one neural signal of the patient. Identification of a specific pathogen in a patient may be based on processing one or more data signals 125. For example, certain signal features are identified in the at least one neural signal and/or the physiological signals (e.g., the heart rate, the respiratory rate, the respiratory phase, electrodermal activity). The certain signal features across the at least one neural signal and/or the physiological signals are compared against historical labels that are associated with the specific pathogen. The historical labels may be specific to the patient, specific to a demographic of the patient, and/or the like.

A specific pathogen may be previously known or unknown. A specific pathogen can be of the type SARS-CoV-2.

In some embodiments, to process the one or more data signals 125, historical labels associated with various immune responses (e.g., infection, cytokine response, response based on a specific pathogen) are accessed. The historical labels may be generated, stored, and/or managed on a platform or database that the system 100 may access via the network 180. In some embodiments, a catalog or library of the historical labels is stored locally on the system 100, such as in data 151.

In some embodiments, a sensor signal (e.g., 135) can include an electrocardiogram signal. A sensor signal (e.g., 135) can include an electroencephalographic signal. A sensor signal (e.g., 135) can include a magnetization signal.

Figure 2:
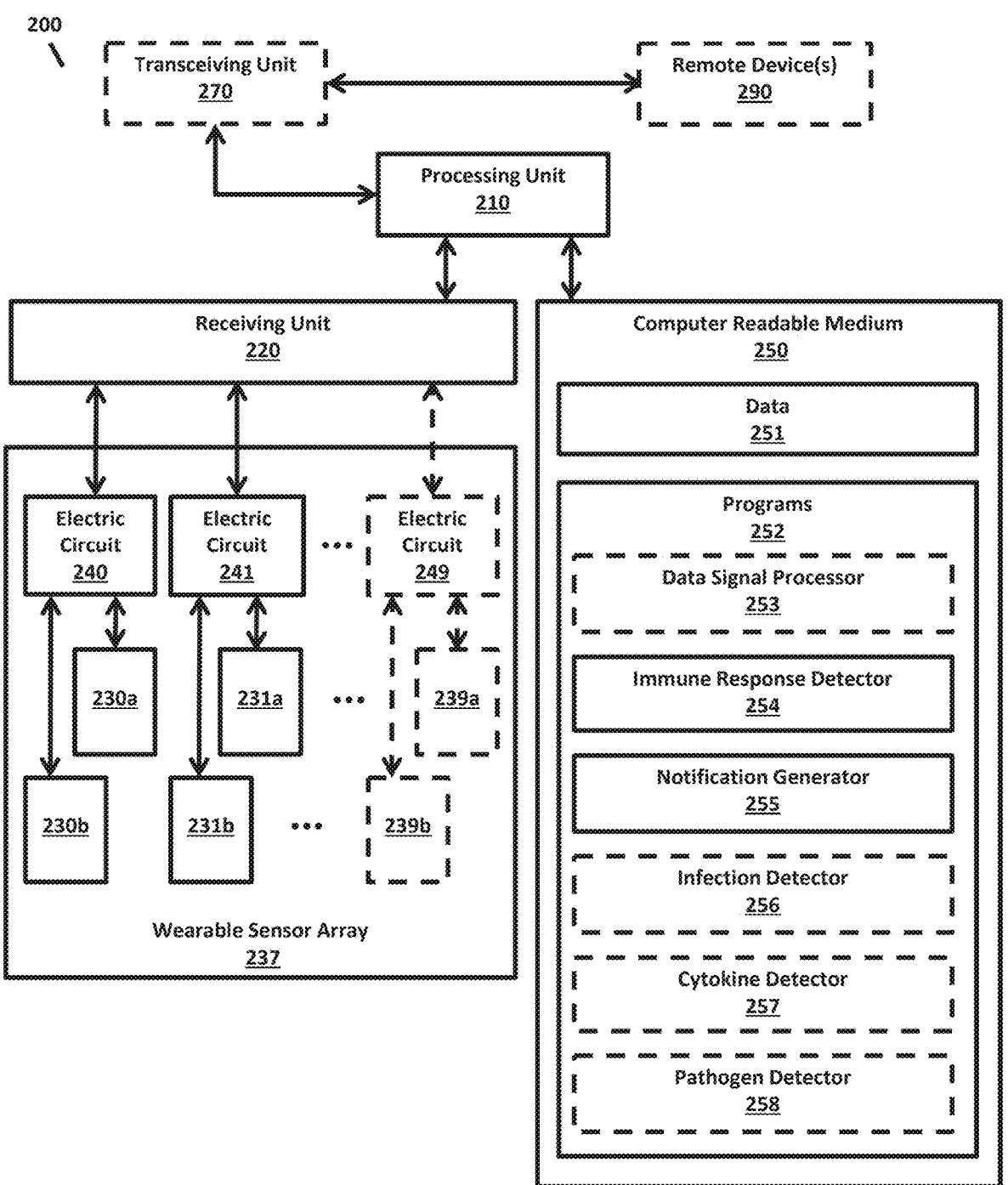
FIG. 2 is a block diagram of another example embodiment of a system for neural signal detection of immune responses in accordance with the disclosed technology.

FIG. 2 is a block diagram of a second example system 200 for neural signal detection of immune responses, consistent with disclosed embodiments, including the system 100. System 200 can include a processing unit 210, a receiving unit 220, a wearable sensor array 237, and a tangible non-transitory computer readable medium 250. The processing unit 210 can include at least one processor. The receiving unit 220 can include at least one receiver. The receiving unit 220 can be configured to receive at least one sensor signal from the wearable sensor array 237. The wearable sensor array 237 can include a plurality of electric circuits (e.g., 240, 241, . . . 249). Each electric circuit can be coupled to two or more sensors (e.g., 230a and 230b, 231a and 231b, . . . 239a and 239b). Sensors (e.g., 230a and 230b, 231a and 231b, . . . 239a and 239b) can be configured to detect at least one neural signal of a patient. Sensors (e.g., 230a and 230b, 231a and 231b, . . . 239a and 239b) can be configured to detect at least one neural signal transcutaneously. At least one of the sensor signals can include at least a portion of a neural signal. The receiving unit 220 can be configured to communicate a data signal to the processing unit 210. The computer readable medium 250 can include data 251 and programs 252. Data 251 can include data corresponding to, for example, electrode signals, data signals, physiological signals, and/or any other data corresponding to a patient. Programs 252 can include instructions. The processing unit 210 can be configured to execute instructions stored in the programs 252. The programs 252 can include an immune response detector 254. The programs 252 can include a notification generator 255. The arrangement of components depicted in FIG. 2 is not intended to be limiting. System 200 can include additional components or fewer components. Multiple components of system 200 may be implemented using the same physical computing device or different physical computing devices.

Some embodiments can include an immune response detector 254. Immune response detector 254 can include instructions configured to cause the processing unit 210 to automatically detect an immune response based at least in part on a data signal. Immune response detector 254 can include instructions configured to cause the processing unit 210 to automatically detect a change in the immune response. For example, the immune response detector 254 include instructions for comparing a data signal against historical labels associated with a normal or resting state of the patient.

Some embodiments can include a notification generator 255. The notification generator 255 can include instructions configured to cause processing unit 210 to automatically create a notification based at least in part on an immune. The notification generator 255 can include instructions configured to cause the processing unit 210 to automatically create a change notification based at least in part on a change in the immune response.

In some embodiments, electric circuits (e.g., 240, 241, . . . 249) can be configured to reduce impedance artifacts. For example, at least a portion of electric circuits (e.g., 240, 241, . . . 249) can be coiled. Each electric circuit (e.g., 240, 241, . . . 249) can include an amplifier.

In some embodiments, the wearable sensor array 237 can include at least one wearable material. A wearable material may be flexible and/or stretchable. The wearable sensor array 237 can include a small contact footprint, e.g., a contact footprint can be of size 15 mm×90 mm. A wearable sensor array 237 can include a low profile, e.g., a profile can have a 2 mm height. A wearable sensor array 237 can be of a light weight, e.g., a weight can be of 1 g or less per sensor. A wearable sensor array 237 can include one or more integrated circuits. A wearable sensor array 237 can include one or more physiological sensors. For example, a surface cup electrode can include a 10 mm diameter. A physiological sensor can be configured to communicate a physiological signal.

In some embodiments, a wearable sensor array 237 can be configured for a minimum and/or maximum spatial resolution. For example, a maximum spatial resolution can be of 2 mm. A wearable sensor array 237 can be configured for a minimum temporal resolution. For example, a minimum temporal resolution can include 270 samples per second.

In some embodiments, a wearable sensor array 237 can include an Optically Pumped Magnetometer (OPM). Each individual OPM sensor in a wearable sensor array 237 can include a footprint of, for example, 12.4 mm×16.6 mm×24.4 mm. An OPM may be configured to sense biological magnetic fields. A biological magnetic field can include one or more neural signals.

In some embodiments, the system 200 can include a transceiving unit 270. The transceiving unit 270 can include at least one transceiver. A transceiver can be configured to communicate with at least one remote device 290. Programs 252 can include instructions configured to cause the processing unit 210 to automatically communicate a notification to a remote device 290 through the employment of transceiving unit 270. A notification can include: an alert, a message, streaming data, and/or any other notifications. A notification can be a change notification. By way of example and not limitation, a remote device 290 may be employed by: a user, a remote operator, a physician, a medical professional, and/or any other user. System 200 can be configured to accept operational instructions from remote device 290.

In some embodiments, programs 252 can include instructions configured to cause the processing unit 210 to automatically communicate a data signal to at least one remote device 290 through the employment of transceiving unit 270.

In some embodiments, programs 252 can include instructions configured to cause the processing unit 210 to automatically receive a data signal from receiving unit 220. A data signal can include one or more sensor signals. A receiving unit 220 can include an amplifier. A receiving unit 220 can be configured to apply one or more filters to one or more sensor signals. A filter can be configured to: remove artifacts, pass high frequencies, pass low frequencies, and/or pass a band of frequencies. A receiving unit 220 can be configured to convert analog sensor signals into digital sensor signals. Programs 252 can include a data signal processor 253. Data signal processor 253 can include instructions configured to cause the processing unit 210 to automatically process a data signal. Processing a data signal can include: filtering, modulating, encoding, converting analog signals to digital, converting digital signals to analog, performing error correction, and/or multiplexing a plurality of signals. A data signal can be processed prior to communication to at least one remote device 290.

In some embodiments, programs 252 can include an infection detector 256. An infection detector 256 can include instructions configured to cause the processing unit 210 to automatically determine that an immune response is based on an infection in a patient. A determination that an immune response is based on an infection in a patient can be based on the detection of at least one neural signal of the patient. A determination that an immune response is based on an infection in a patient may be based on a heart rate, a respiratory rate, a respiratory phase, and/or electrodermal activity of the patient. For example, at least one neural signal may be detected and/or analyzed at peak inspiration of a respiratory cycle in a patient. Thus, in some embodiments, the neural signal is correlated with a physiological signal of the patient in order to identify certain signal features of the neural signal. A determination that an immune response is based on an infection in a patient can be based on processing one or more data signals. For example, certain signal features are identified in the at least one neural signal and/or the physiological signals (e.g., the heart rate, the respiratory rate, the respiratory phase, electrodermal activity). The certain signal features across the at least one neural signal and/or the physiological signals are compared against historical labels that are associated with past immune responses based on infections. The historical labels may be specific to the patient, specific to a demographic of the patient, and/or the like.

In some embodiments, programs 252 can include a cytokine detector 257. A cytokine detector 257 can include instructions configured to cause a processing unit 210 to automatically determine that an immune response is based on a cytokine response in a patient. Cytokine detector 257 can include instructions configured to cause a processing unit 210 to automatically determine that a cytokine response is based on a specific cytokine, cytokine concentration, and/or cytokine type. A determination that an immune response is based on a cytokine response in a patient may be based on the detection of at least one neural signal of the patient. A determination that an immune response is based on a cytokine response in a patient can be based on a heart rate, a respiratory rate, a respiratory phase, and/or electrodermal activity of the patient. For example, at least one neural signal can be detected and/or analyzed at peak inspiration of a respiratory cycle in a patient. Thus, in some embodiments, the neural signal is correlated with a physiological signal of the patient in order to identify certain signal features of the neural signal. A determination that an immune response is based on a cytokine response in a patient may be based on processing one or more data signals. For example, certain signal features are identified in the at least one neural signal and/or the physiological signals (e.g., the heart rate, the respiratory rate, the respiratory phase, electrodermal activity). The certain signal features across the at least one neural signal and/or the physiological signals are compared against historical labels that are associated with past cytokine responses. The historical labels may be specific to the patient, specific to a demographic of the patient, and/or the like.

In some embodiments, programs 252 can include a pathogen detector 258. A pathogen detector 258 can include instructions configured to cause a processing unit 210 to automatically determine that an immune response is based on a pathogen in a patient. A determination that an immune response is based on a pathogen in a patient can be based on the detection of at least one neural signal of the patient. A determination that an immune response is based on a pathogen in a patient may be based on processing one or more data signals. A pathogen detector 258 can include instructions configured to cause a processing unit 210 to automatically identify a specific pathogen in a patient. The identification of a specific pathogen in a patient can be based on the detection of at least one neural signal, physiological signal, or combination thereof derived from the patient. Identification of a specific pathogen in a patient can be based on processing one or more data signals. The specific pathogen can be previously known or unknown. The specific pathogen can be of SARS-CoV-2. For example, certain signal features are identified in the at least one neural signal and/or the physiological signals (e.g., the heart rate, the respiratory rate, the respiratory phase, electrodermal activity). The certain signal features across the at least one neural signal and/or the physiological signals are compared against historical labels that are associated with the specific pathogen. The historical labels may be specific to the patient, specific to a demographic of the patient, and/or the like.

In some embodiments, a system (e.g., 100, 200) for neural signal detection of immune responses can be wearable. The system can include wearable components. For example, a processing unit (e.g., 110, 210) can be wearable. The processing unit can be physically connected to a wearable sensor array (e.g., 237). For example, a receiving unit (e.g., 120, 220) may be wearable. The receiving unit can be physically connected to a wearable sensor array (e.g., 237). For example, a computer readable medium (e.g., 150, 250) can be wearable. The computer readable medium can be physically connected to a wearable sensor array (e.g., 237). For example, a transceiving unit (e.g., 170, 270) can be wearable. The transceiving unit can be physically connected to a wearable sensor array (e.g., 237).

In some embodiments, a receiving unit (e.g., 120, 220) can include a transmitter. The transmitter can be configured to transmit one or more data signals to a processing unit (e.g., 110, 210). For example, a processing unit (e.g., 110, 210) can be part of a computing system such as a personal computer, a smartphone, a tablet, a wearable computing system, and/or any other computing system. The computing system can include a computer readable medium (e.g., 150, 250). The computing system can include a transceiving unit (e.g., 170, 270).

In some embodiments, a receiving unit (e.g., 120, 220) can be configured to detect at least one neural signal in one or more of the followings: a vagus nerve of a patient, a sympathetic nerve of a patient, a spinal nerve of a patient, and/or any other neural structure of the patient. A receiving unit (e.g., 120, 220) can be configured to detect changes in at least one neural signal in one or more of the followings: a vagus nerve of the patient, a sympathetic nerve of a patient, a spinal nerve of the patient, and/or any other neural structure of the patient. A receiving unit (e.g., 120, 220) can be configured to differentiate between a plurality of neural signals. For example, each of at least some of a plurality of neural signals can include a distinct frequency. For example, at least some of a plurality of neural signals can include a distinct firing pattern or nested firing frequency. For example, each of at least some of a plurality of neural signals can include a distinct amplitude. A plurality of neural signals can originate from a plurality of neurons. A plurality of neurons can include one or more groups of neurons.

In some embodiments, clustering techniques are used to compare and differentiate between neural signals. For example, given a plurality of neural signals, t-distributed stochastic neighbor embedding (T-SNE) is performed for dimensionality reduction on each neural signal. Subsequently, a clustering algorithm is trained and used to cluster the reduced-dimension neural signals.

In some embodiments, a receiving unit (e.g., 120, 220) can be configured to detect at least one physiological signal of the patient. A receiving unit (e.g., 120, 220) can be configured to detect at change in least one physiological signal. A receiving unit (e.g., 120, 220) can be configured to differentiate between a plurality of physiological signals. For example, each of at least some of a plurality of physiological signals can include a distinct frequency. For example, at least some of a plurality of physiological signals can include a distinct firing pattern. For example, each of at least some of a plurality of physiological signals can include a distinct amplitude.

In some embodiments, a system (e.g., 100, 200) can be configured to differentiate between a plurality of neural signals from a patient. For example, the system (e.g., 100, 200) can be configured to differentiate a first vagus or sympathetic nerve waveform from a second vagus or sympathetic nerve waveform. With the differentiation, the system (e.g., 100, 200) is configured to determine a change in immune response based on a change in nerve waveform or signal. In some examples, the system (e.g., 100, 200) uses a data model (e.g., a machine learning model) to determine whether a significant change exists between two nerve signals. A system (e.g., 100, 200) can be configured to compare one or more neural signals to one or more previous neural signals. A previous neural signal can be from the same patient or from one or more other patients. A previous neural signal may be classified as an immune response to a specific pathogen and/or disease. The system (e.g., 100, 200) can be configured to differentiate a waveform according to one neural structure from waveforms according to other neural structures. For example, the system (e.g., 100, 200) can be configured to differentiate a vagus or sympathetic nerve waveform according to a neural waveform from another neural structure.

In some embodiments, a system (e.g., 100, 200) can be configured to differentiate between a plurality of physiological signals from a patient. For example, the system (e.g., 100, 200) can be configured to differentiate a first physiological waveform from a second physiological waveform. A system (e.g., 100, 200) can be configured to compare one or more physiological signals to one or more previous physiological signals. A previous physiological signal can be from the same patient or from one or more other patients. A previous physiological signal can be classified as an immune response to a specific pathogen and/or disease.

In some embodiments, a system (e.g., 100, 200) can be configured to detect a change in at least one neural signal of a patient. The change can be based on a change in frequency from a previous neural signal from the patient. For example, a firing frequency of a neural signal can be distinct from a firing frequency of a previous neural signal from the patient. The change can be based on a change in amplitude from a previous neural signal from the patient. For example, an amplitude of a neural signal can be distinct from an amplitude of a previous neural signal from the patient. The change can be based on a change in firing frequencies from a plurality of previous neural signals from the patient. For example, firing frequencies of a plurality of neural signals may be distinct from firing frequencies of a plurality of previous neural signals from the patient. Signal features other than firing frequency or amplitude can be compared against historical labels, or aspects of previous neural signals. A previous neural signal from a patient can include one or more neural signals captured during a resting state of the patient. Detection of a change in a neural signal of a patient can be based on a heart rate, a respiratory rate, a respiratory phase, and/or electrodermal activity of the patient.

In some embodiments, a system (e.g., 100, 200) for neural signal detection of immune responses can be configured to determine when one or more neural signals crosses a threshold. For example, the system (e.g., 100, 200) can be configured to determine when a neural signal crosses a cytokine to neural signal threshold. A cytokine to neural signal threshold can be based on one or more specific cytokines, cytokine concentrations, and/or cytokine types. The determination of a neural signal crossing a cytokine to neural signal threshold may indicate an immune response to inflammation. For example, the system (e.g., 100, 200) can be configured to determine when a firing frequency of one or more neural signals crosses a firing frequency threshold. For example, the system (e.g., 100, 200) can be configured to determine when a spike frequency of one or more neural signals crosses a spike frequency threshold. For example, the system (e.g., 100, 200) may be configured to determine when a spike amplitude of one or more neural signals crosses a neural signal spike amplitude threshold.

In some embodiments, a system (e.g., 100, 200) for neural signal detection of immune responses can be configured to determine when one or more physiological signals crosses a threshold. For example, the system (e.g., 100, 200) can be configured to determine when one or more respiratory signals crosses a respiratory signal spike amplitude threshold. For example, the system (e.g., 100, 200) can be configured to determine when high and/or low respiratory spikes in one or more respiratory signals crosses a respiratory phase threshold. For example, the system (e.g., 100, 200) can be configured to determine when high and/or low respiratory spikes in one or more respiratory signals remains over a respiratory phase threshold for a pre-determined amount of time. Accordingly, the system (e.g., 100, 200) is configured to use signal features of both neural signals and physiological signals to identify an immune response in a patient or subject.

In some embodiments, a system (e.g., 100, 200) for neural signal detection of immune responses can include a neural classifier. A neural classifier can include instructions configured to cause a processing unit (e.g., 110, 210) to automatically classify one or more features or aspects of one or more neural signals into classified data. A neural classifier may be based on one or more data models. Features of neural signals can include: a frequency, a change in frequency, an amplitude, a change in amplitude, and/or any other aspects of a waveform of one or more neural signals. At least these features of neural signals are identified using various processing techniques. For example, an amplitude thresholding method is used to detection neural spikes of neural signals.

Features or aspects of neural signals can be classified according to one or more of the following causes of an immune response: inflammation, an infection, a cytokine response, a specific pathogen, and/or a specific disease. Classification of a feature of a neural signal can include identification of the feature from one or more data signals. Classification of a feature of a neural signal can be based on one or more features of one or more physiological signals.

Classification of a feature of a neural signal can be based on a resting state of a patient. Classification of a feature of a neural signal can include correlating an identified feature of a neural signal with data from one or more data models.

Some embodiments can include one or more data models. A data model can be configured to organize any combination of the following: features of neural signals, causes of an immune response in a patient, and/or features of one or more physiological signals. A data model can include one or more labels. A label may be employed to correlate features of neural signals with known pathogens and/or diseases. A label may be employed to correlate features of neural signals with known blood cytokine concentration. A known blood cytokine concentration may be specific to one or more specific cytokines, cytokine concentrations, and/or cytokine types. A label can be employed to correlate features of neural signals with features of physiological signals. A data model can be expanded. Expansion of a data model can be based on new labeled samples. New labeled samples can be labeled based on neural signals from one or more patients. Labeled samples can include an additional class of data. The one or more data models may include a machine learning model, deep learning model, deep neural network, and/or the like that is trained via the labels that are correlated or associated with known immune responses (e.g., known pathogens, known diseases, known cytokine concentrations) to predict whether a neural signal and/or a physiological signal (and signal features thereof) are indicative of a known immune response.

In some embodiments, classified data may be employed to correlate one or more neural signals with one or more of the following causes of an immune response: inflammation, an infection, a cytokine response, a specific pathogen, and/or a specific disease. Classified data can be shared with one or more systems. Classified data can be available to one or more systems. Classified data can be based on data signals from one or more systems. Classified data can be stored in cloud-based databases and/or system-based databases (e.g., data 151, 251). Classified data can be compared to data index libraries previously acquired. For example, the classified data includes labels corresponding to known immune responses that are determined based on previous monitoring of neural signals and/or physiological signals during a known immune response.

In some embodiments, the classified data is generated using optically pumped magnetometers (OPMs). For example, OPMs are adhered to skin surface of subjects experiencing a known immune response, and the OPMs are configured to collect neural signals and/or physiological signals during the known immune response. In some embodiments, the OPMs are used in an absolute zero magnetic field environment, such as a magnetically shielded room.

Some embodiments can include an immune response detector (e.g., 154, 254). An immune response detector (e.g., 154, 254) can include instructions configured to cause a processing unit (e.g., 110, 210) to automatically employ classified data to detect an immune response. An immune response detector (e.g., 154, 254) can include instructions configured to cause a processing unit (e.g., 110, 210) to automatically employ classified data to detect a change in an immune response.

Some embodiments include an infection detector (e.g., 156, 256). An infection detector (e.g., 156, 256) can include instructions configured to cause a processing unit (e.g., 110, 210) to automatically employ classified data to determine that an immune response is based on an infection in a patient.

Some embodiments can include a cytokine detector (e.g., 157, 257). A cytokine detector (e.g., 157, 257) can include instructions configured to cause a processing unit (e.g., 110, 210) to automatically employ classified data to determine that an immune response is based on a cytokine response in a patient. A cytokine detector (e.g., 157, 257) can include instructions configured to cause a processing unit (e.g., 110, 210) to automatically determine that a cytokine response is based on a specific cytokine, cytokine concentration, and/or cytokine type.

Some embodiments can include a pathogen detector (e.g., 158, 258). A pathogen detector (e.g., 158, 258) can include instructions configured to cause a processing unit (e.g., 110, 210) to automatically employ classified data to determine that an immune response is based on a specific pathogen in a patient.

Some embodiments can include a physiological signal. A physiological signal can include a heart rate signal, an electrocardiogram (ECG) signal, an electroencephalographic (EEG) signal, and/or any other physiological signal. A physiological signal can have at least one data stream including measurements of respiratory rate, respiratory phase, heart rate, cortical potential, skin conductance response, laser Doppler shift, impedance pneumography potential, skin temperature, respiratory bio-acoustic signal, and/or any other physiological measurements. By way of example and not limitation, position can be chest position, chest displacement, chest movement, and/or any other measured position. A physiological signal can be synchronized with one or more other physiological signals and/or one or more neural signals.

Some embodiments may include a physiological sensor. In some embodiments, for example, the physiological sensor can include a heart rate sensor, at least one scalp electrode, at least one skin conductance electrode, at least one photodetector, at least one avalanche photodiode, a respiration rate sensor, at least one thermistor, at least one thermometer, at least one thermocouple, and/or any other physiological sensors. A heart rate sensor can be configured to measure heart rate electrically and/or optically. A heart rate sensor may be configured to measure Heart Rate Variability (HRV), which may be determined by a receiving unit (e.g., 120, 220) and/or a processing unit (e.g., 110, 210) based on a heart rate signal communicated from a heart rate sensor. Physiological sensors configured to measure HRV can be coupled to a wearable sensor array (e.g., 237), a chest strap, and/or a wrist band. A chest strap and/or wrist band can be coupled to at least one additional physiological sensor configured to measure, for example, breathing rate, galvanic skin response, skin temperature, and/or any other physiological measurements. A photodetector can be configured to measure laser Doppler shift. Similarly, an avalanche photodiode can be configured to measure laser Doppler shift. A respiration rate sensor can include at least one impedance pneumography electrode, at least one capacitive sensor, at least one piezoelectric sensor, at least one servo, an acoustic transducer, an inclinometer, an accelerometer, and/or any other respiration rate sensor. Respiration rate may be estimated from HRV and/or a photoplethysmography (PPG). A physiological sensor can be configured to measure sympathetic tone. Sympathetic tone can be relative to previous measurements. A physiological sensor can be configured to measure parasympathetic tone. Parasympathetic tone may be relative to previous measurements. A physiological sensor may be wearable. A physiological sensor may be configured to communicate data in more than one-time scale. Data communicated from a physiological sensor can be recorded in a fixed time scale, in more than one-time scale, in one adjustable time scale, and/or in a plurality of adjustable time scales. A physiological sensor can be a tattoo-based sensor or a skin-applied electrochemical sensor.

In some embodiments, a system (e.g., 100, 200) can include at least one biofuel cell that can be configured to power at least a portion of a system. The biofuel cell can be wearable.

In some embodiments, at least a portion of a system (e.g., 100, 200) can be configured as a System on a Chip (SoC). A system (e.g., 100, 200) can include a signal conditioning circuitry. A system (e.g., 100, 200) can include an integrated power management circuitry.

Figure 3:
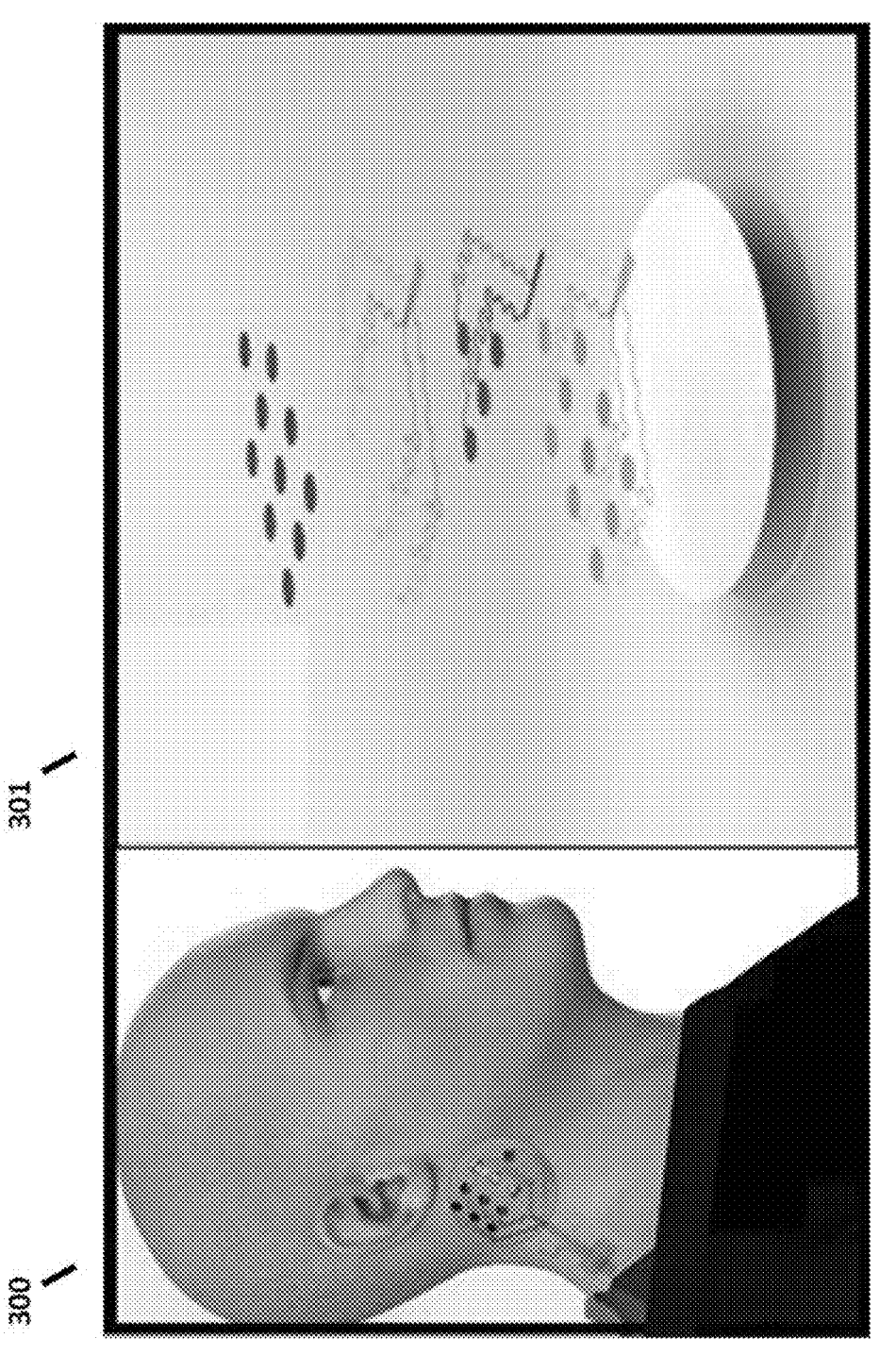
FIG. 3 illustrates an example wearable sensor array in accordance with example embodiments of the disclosed technology.

FIG. 3 illustrates an example wearable sensor array 301, consistent with disclosed embodiments. A wearable sensor array 301 can include a plurality of sensors, a plurality of electric circuits, a plurality of electrode circuits, and/or a plurality of optically pumped magnetometer circuit. Wearable sensor array 301 can be configured to be worn by patient 300. A wearable sensor array 301 can be part of a system that is configured to be worn by patient 300. Wearable sensor array 301 can be configured to be worn over a section of a vagus nerve or sympathetic nerve of patient 300 (as shown in FIG. 3). For example, the wearable sensor array 301 is worn at the cervical neck of the patient 300, where there is a confluence of both afferent and efferent autonomic neuron fibers that relay information to multiple organs. Wearable sensor array 301 can be configured to be worn by patient 300 through the employment of one or more adhesives. Wearable sensor array 301 can be configured to be worn over a section of a spinal nerve of patient 300. Wearable sensor array 301 can be configured to be worn over at least a section of any neural structure of patient 300. Wearable sensor array 301 can be configured to detect at least one neural signal transcutaneously.

Figure 4:
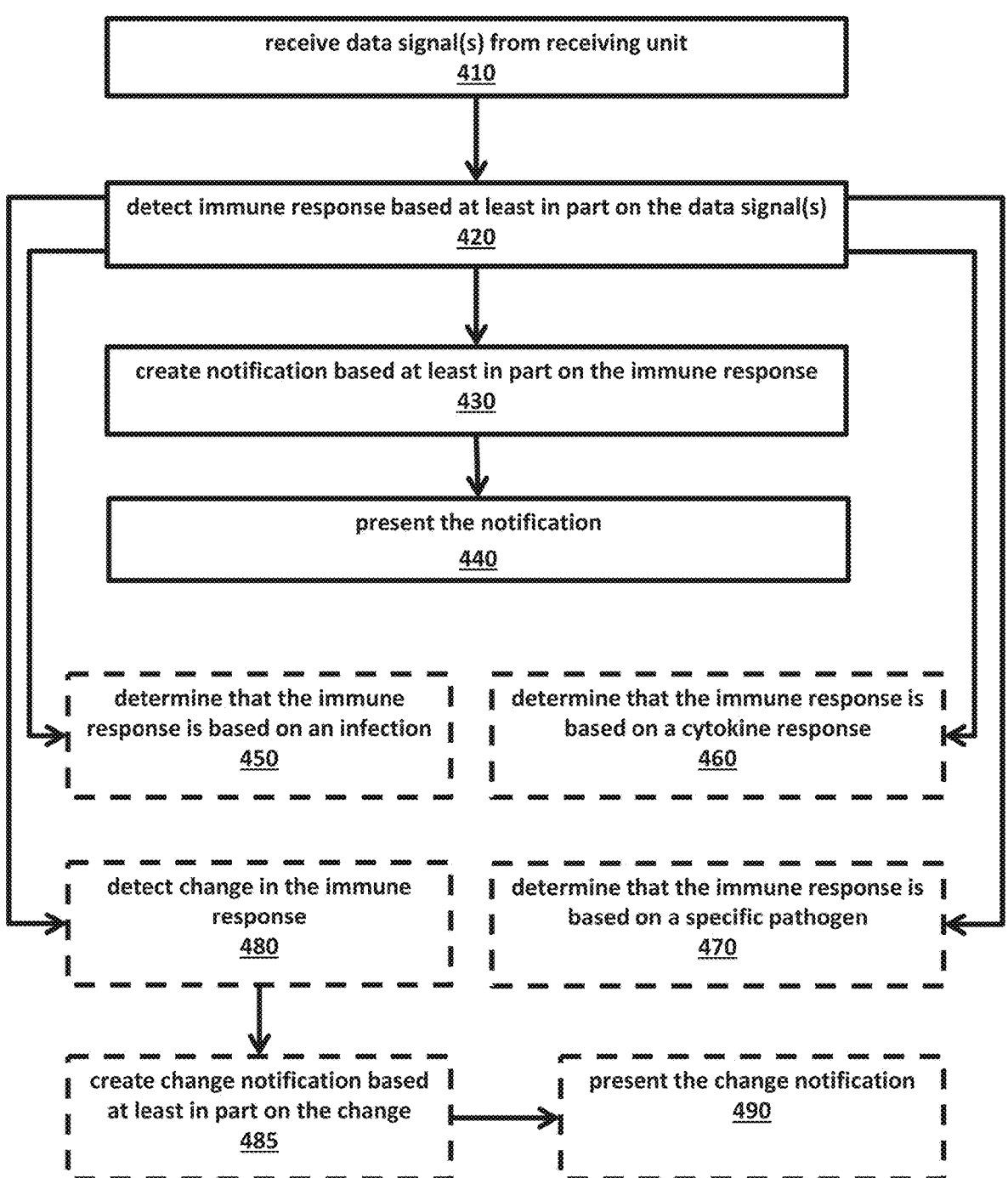
FIG. 4 is a flow diagram of an example embodiment of a method for neural signal detection of immune responses in accordance with the disclosed technology.

FIG. 4 illustrates a flow diagram of a first example process for neural signal detection of immune responses, consistent with disclosed embodiments. Data signal(s) can be received from a receiving unit at 410. The data signal(s) can include one or more sensor signals. One or more sensor signals can be communicated from one or more wearable sensors that can be configured to detect at least one neural signal transcutaneously. The sensor signals may further be configured to enable detection of physiological signals. An immune response can be detected at 420. The detection of the immune response may be based at least in part on the data signal(s). For example, signal features of the at least one neural signal and/or physiological signals are compared against signal labels or previously identified features known to be associated with an immune response. An infection can be determined at 450. Determination of the infection can be based on the immune response and/or at least in part on the data signal(s). A cytokine response can be determined at 460. Determination of the cytokine response can be based on the immune response and/or at least in part on the data signal(s). A specific pathogen may be determined at 470. The determination of the specific pathogen can be based on the immune response and/or at least in part on the data signal(s). For example, in each of 450, 460, and 470, signal features of the at least one neural signal and/or physiological signals are compared against signal labels or previously identified features known to be associated with infections, cytokine responses (e.g., cytokine concentrations), and/or specific pathogens. In some embodiments, a classifier and/or model (e.g., a machine learning model) is configured or trained to detect the immune response, infection, cytokine response, or specific pathogen based on an input of signal features of neural signals and/or physiological signals.

A notification may be created at 430. Creation of a notification can be based at least in part on the immune response and/or at least in part on determination of an infection. Creation of a notification may be based at least in part on determination of a cytokine response and/or at least in part on determination of a specific pathogen. The notification may be presented at 440. A change in the immune response may be detected at 480. The detection of the change in the immune response may be based on the immune response and/or at least in part on the data signal(s). A change notification can be created at 485. The creation of the change notification can be based at least in part on the change in the immune response. The change notification can be presented at 490.

Figure 5:
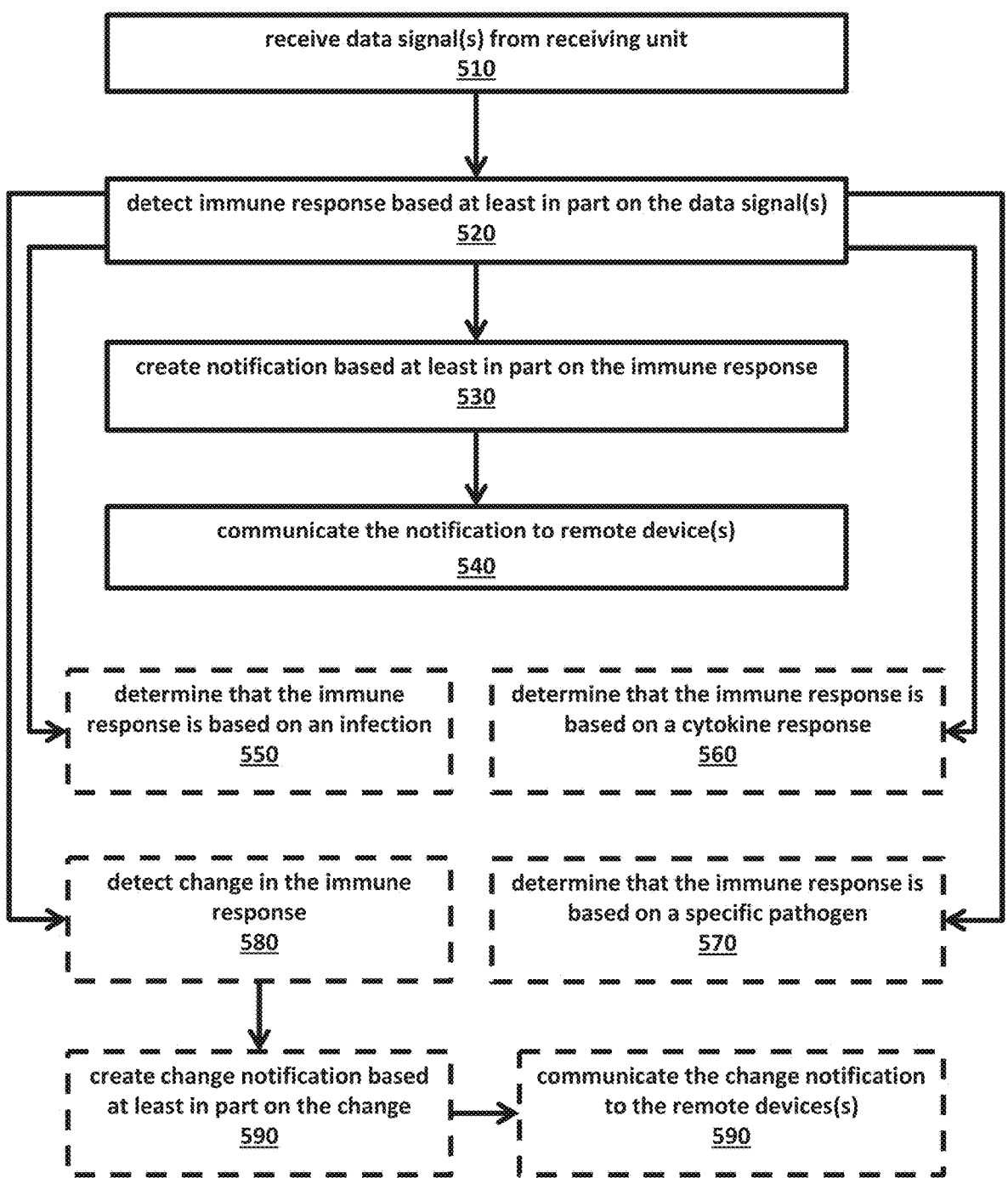
FIG. 5 is a flow diagram of another example embodiment of a method for neural signal detection of immune responses in accordance with the disclosed technology.

FIG. 5 is a flow diagram of a second example process for neural signal detection of immune responses, consistent with disclosed embodiments. Data signal(s) can be received from a receiving unit at 510. Data signal(s) can include one or more sensor signals that can be communicated from one or more wearable sensors. The wearable sensor(s) can be configured to detect at least one neural signal transcutaneously. An immune response may be detected at 520. The detection of the immune response can be based at least in part on the data signal(s). An infection can be determined at 550. The determination of the infection can be based on the immune response and/or at least in part on the data signal(s). A cytokine response can be determined at 560. The determination of the cytokine response can be based on the immune response and/or at least in part on the data signal(s). A specific pathogen can be determined at 570. The determination of the specific pathogen can be based on the immune response and/or at least in part on the data signal(s). A notification can be created at 530. The creation of the notification can be based at least in part on the immune response, and/or at least in part on determination of an infection, and/or at least in part on determination of a cytokine response, and/or at least in part on determination of a specific pathogen. The notification may be communicated to one or more remote devices at 540. A change in the immune response may be detected at 580. The detection of the change in the immune response can be based on the immune response and/or at least in part on the data signal(s). A change notification may be created at 585. The creation of the change notification can be based at least in part on the change in the immune response. The change notification can be communicated to one or more remote devices at 590.

Figure 6:
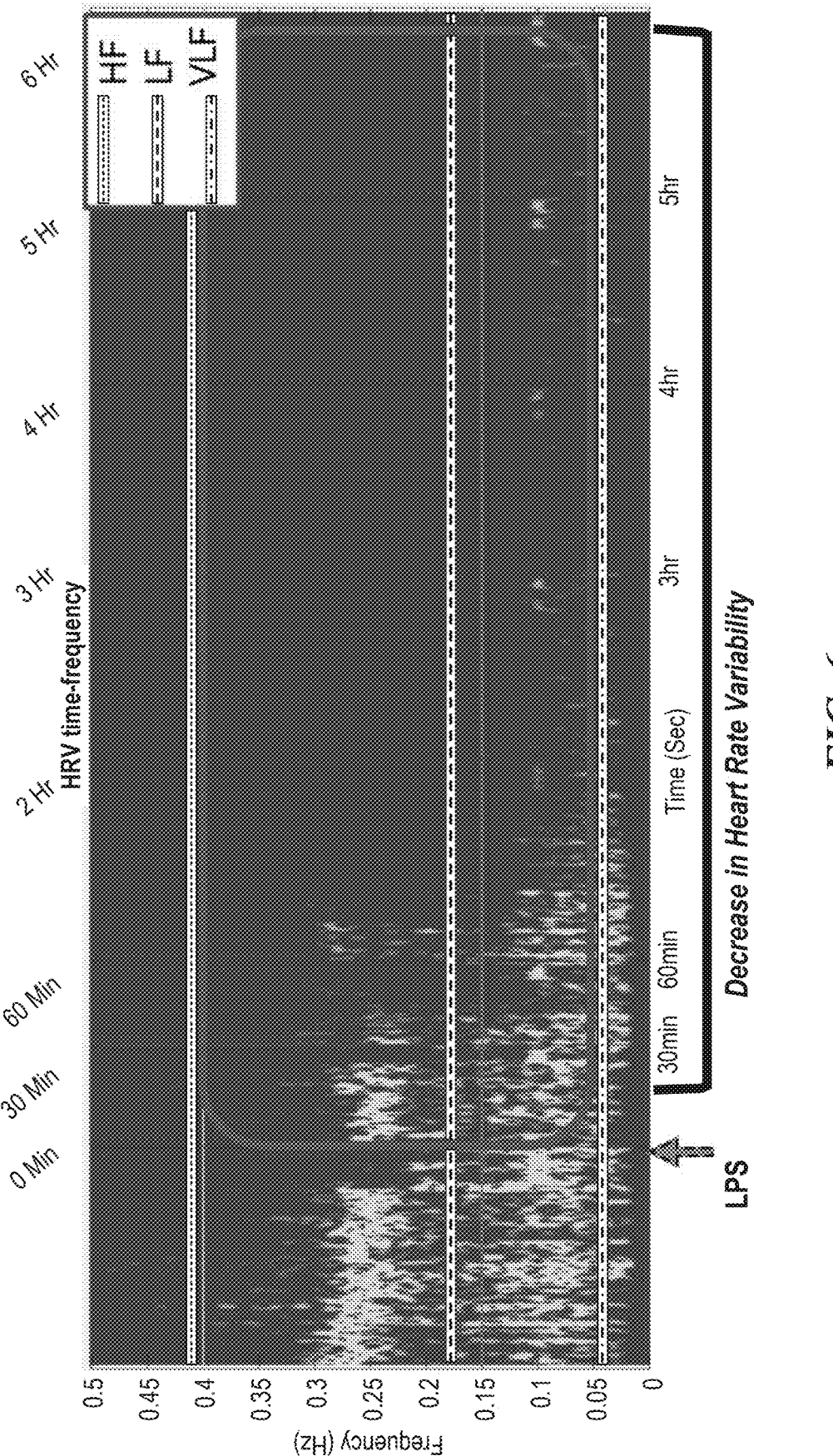
FIG. 6 is a data plot of a physiological signal from a first patient in response to an LPS injection with a known bacterium.

FIG. 6 is a data plot of a physiological signal from a first patient in response to an LPS injection with a known bacteria, consistent with disclosed embodiments. At least some of the data (e.g., 151, 251) presented in the data plot may have originated from the physiological signal. The physiological signal can include a heart rate signal of the first patient. The heart rate signal may have been communicated from a heart rate sensor. The data plot can present heart rate variability of the first patient. For example, the data plot of FIG. 6 demonstrates that heart rate variability decreases for a duration of time after the LPS injection. According to the decrease in heart rate variability in the physiological signal of the first patient in response to the known bacteria, a historical label can be generated to indicate a correlation between the decrease in heart rate variability with an immune response to the known bacteria.

An immune response detector (e.g., 154, 254) can include instructions configured to cause a processing unit (e.g., 110, 210) to automatically detect an immune response based at least in part on the physiological signal. For example, historical labels are generated from the physiological signal in response to the known bacteria, and the historical labels are associated with the known bacteria. The immune response detector (e.g., 154, 254) is configured to automatically detect an immune response based on comparing signal features of a given physiological signal with the historical labels of the illustrated physiological signal.

Figure 7:
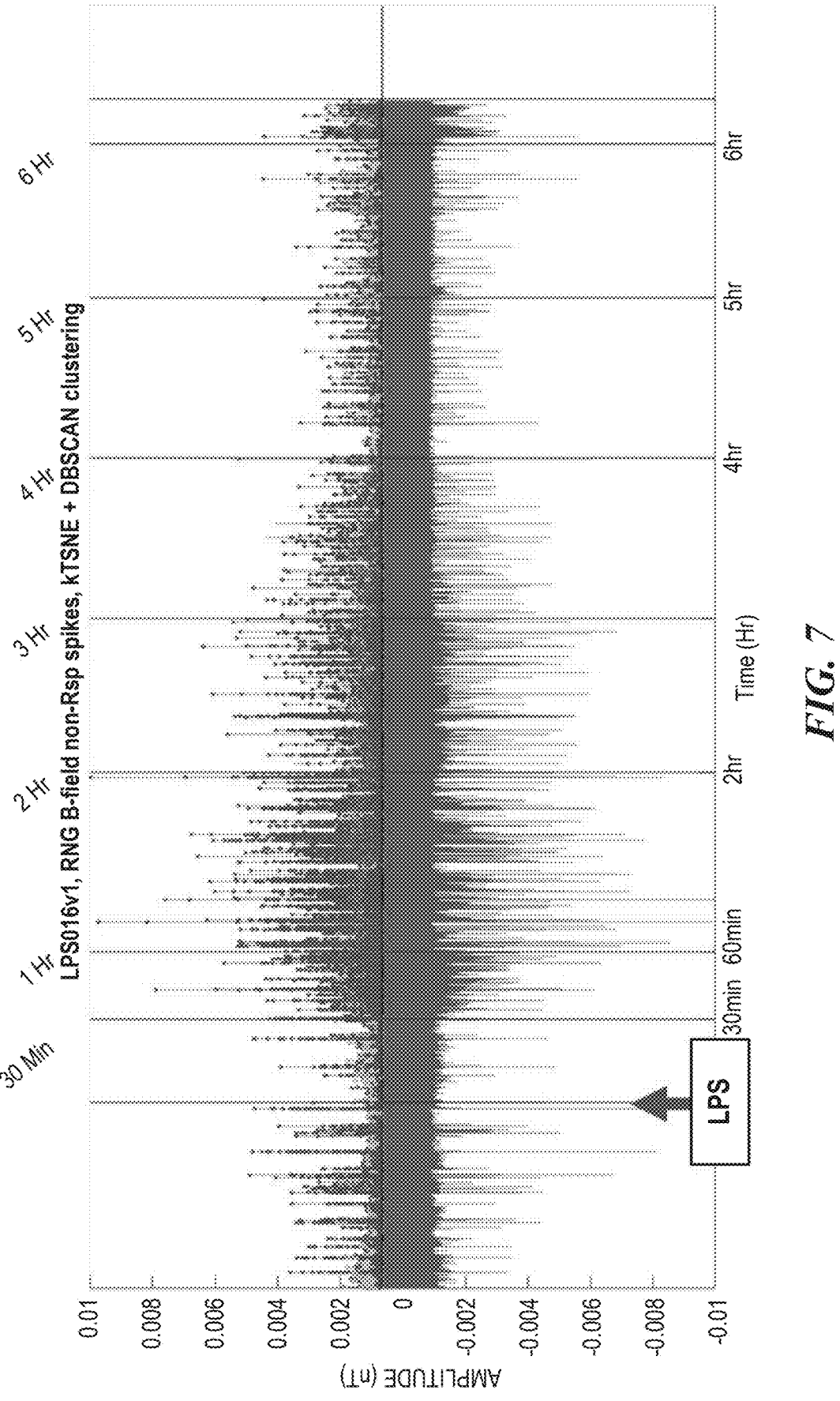
FIG. 7 is a data plot of a neural signal from a first patient in response to an LPS injection with a known bacterium.

FIG. 7 is a data plot of a neural signal from a first patient in response to an LPS injection with a known bacteria, consistent with disclosed embodiments. At least some of the data (e.g., 151, 251) presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the first patient. The data plot can present a distinct firing pattern, a nested firing frequency, and/or a plurality of amplitudes for the one or more sensor signals. For example, the data plot in FIG. 7 demonstrates that neural spike frequency and spike amplitude increases for a duration of time after the LPS injection. A historical label can be generated to indicate a correlation between the increase in neural spike frequency and spike amplitude and the immune response of the first patient to the known bacteria.

An immune response detector (e.g., 154, 254) can include instructions configured to cause a processing unit (e.g., 110, 210) to automatically detect an immune response based at least in part on the one or more sensor signals. For example, historical labels are generated from the neural signal in response to the known bacteria, and the historical labels are associated with the known bacteria. The immune response detector (e.g., 154, 254) is configured to automatically detect an immune response based on comparing signal features of a given neural signal with the historical labels of the illustrated neural signal.

Figure 8:
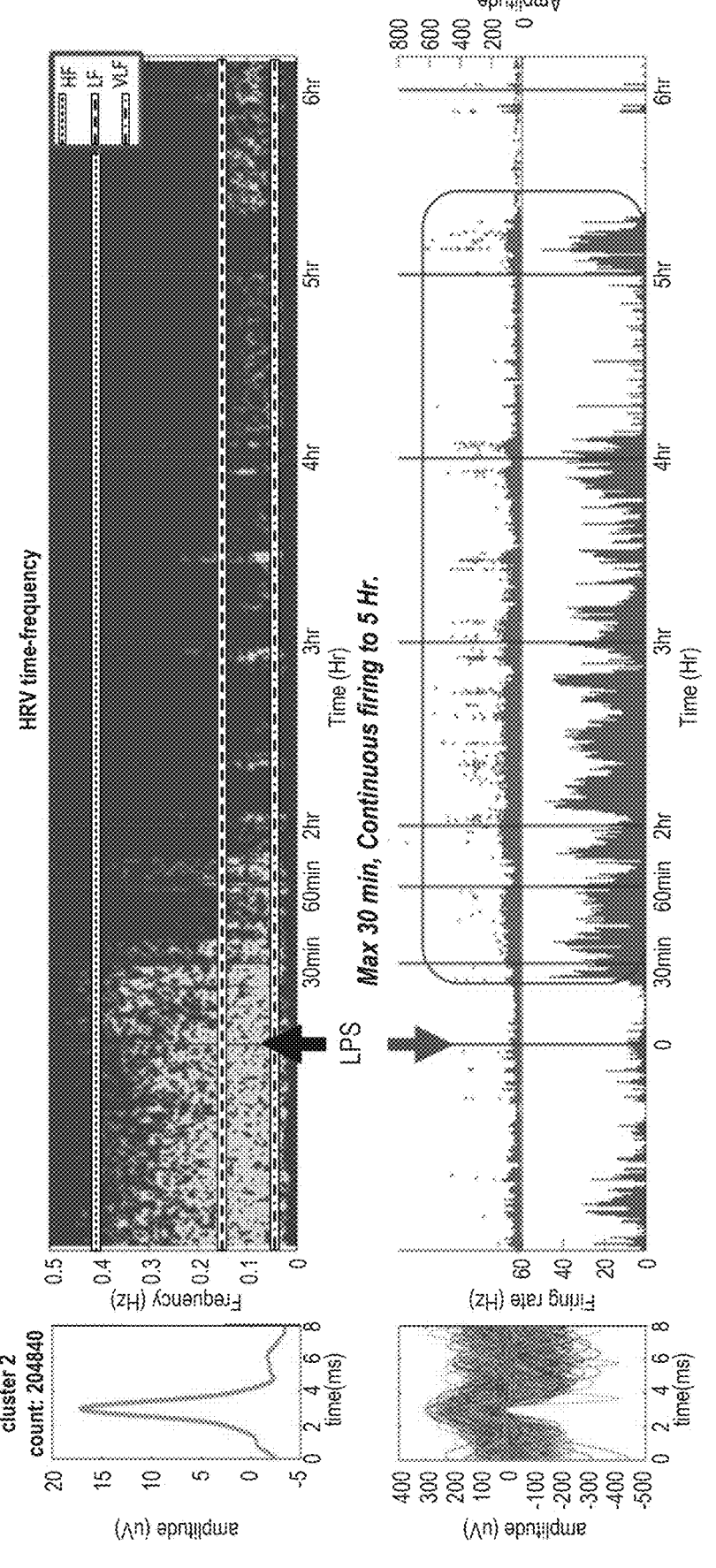
FIG. 8 is a data plot correlating a physiological signal to a neural signal from a patient in response to an LPS injection with a known bacterium.

FIG. 8 is a data plot correlating a physiological signal to a neural signal from a patient in response to an LPS injection with a known bacteria, consistent with disclosed embodiments. At least some of the data (e.g., 151, 251) presented in the data plot may have originated from a physiological signal. The physiological signal can include a heart rate signal of the patient. The heart rate signal may have been communicated from a heart rate sensor. The data plot can present heart rate variability of the patient. At least some of the data presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the patient. The data plot can present a distinct firing pattern, a nested firing frequency, and/or a plurality of amplitudes for the one or more sensor signals. An immune response detector (e.g., 154, 254) can include instructions configured to cause a processing unit (e.g., 110, 210) to automatically detect an immune response based at least in part on the physiological signal and/or the one or more sensor signals. For example, a historical label across the neural signal and the physiological signal that are correlated by time is generated and associated with the known bacteria. Based on identifying the historical label across a given neural signal and a given physiological signal, the immune response detector (e.g., 154, 254) can automatically detect an immune response and predict the presence of the known bacteria.

Figure 9:
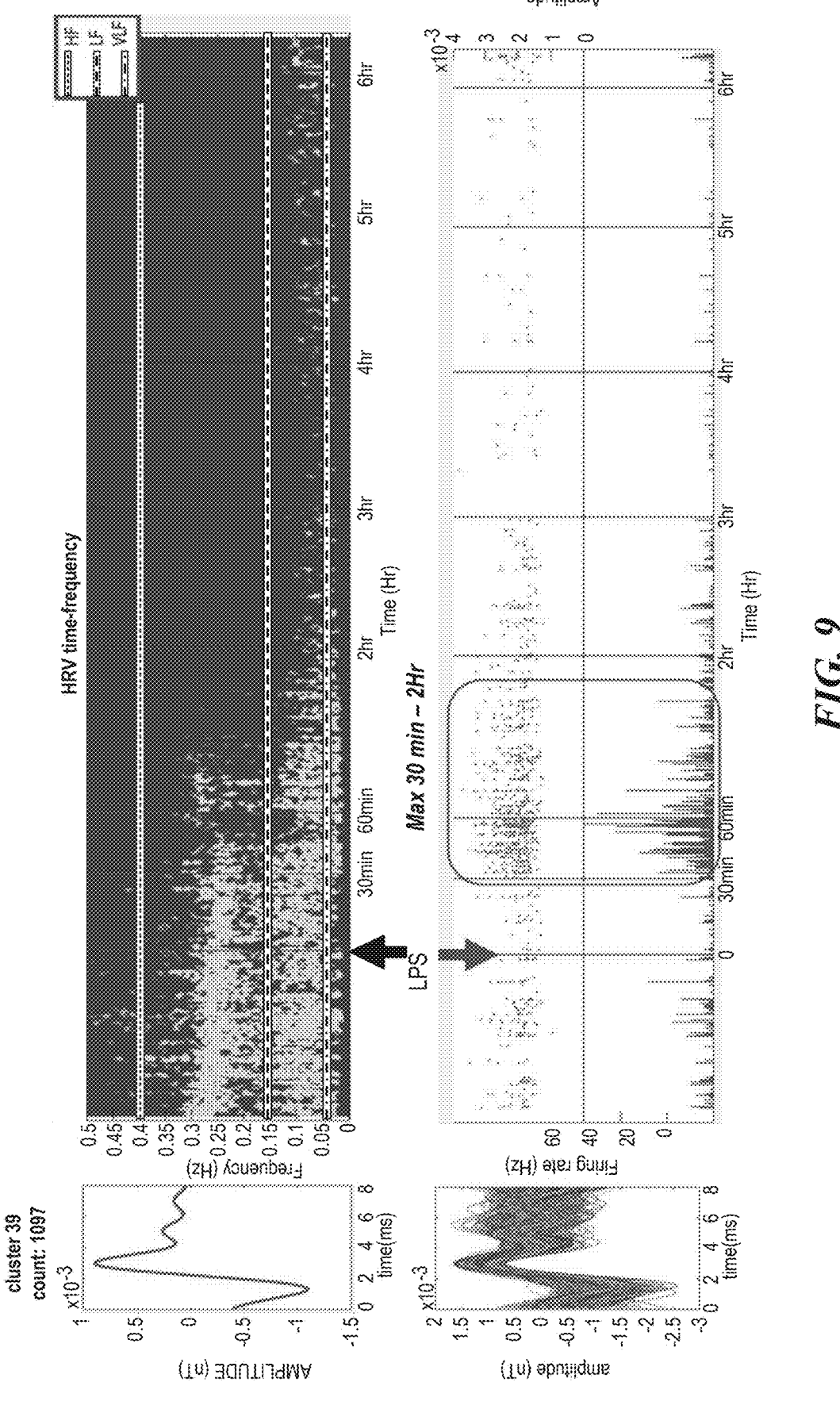
FIG. 9 is a data plot correlating a physiological signal to a neural signal from a first patient over a second duration in response to an LPS injection with a known bacterium.

FIG. 9 is a data plot correlating a physiological signal to a neural signal from a first patient over a second duration in response to an LPS injection with a known bacteria, consistent with disclosed embodiments. At least some of the data (e.g., 151, 251) presented in the data plot may have originated from a physiological signal. The physiological signal can include a heart rate signal of the first patient. The heart rate signal may have been communicated from a heart rate sensor. The data plot can present heart rate variability of the first patient. At least some of the data presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the first patient. The data plot can present a distinct firing pattern, a nested firing frequency, and/or a plurality of amplitudes for the one or more sensor signals. An immune response detector (e.g., 154, 254) can include instructions configured to cause a processing unit (e.g., 110, 210) to automatically detect an immune response based at least in part on the physiological signal and/or the one or more sensor signals.

Figure 10:
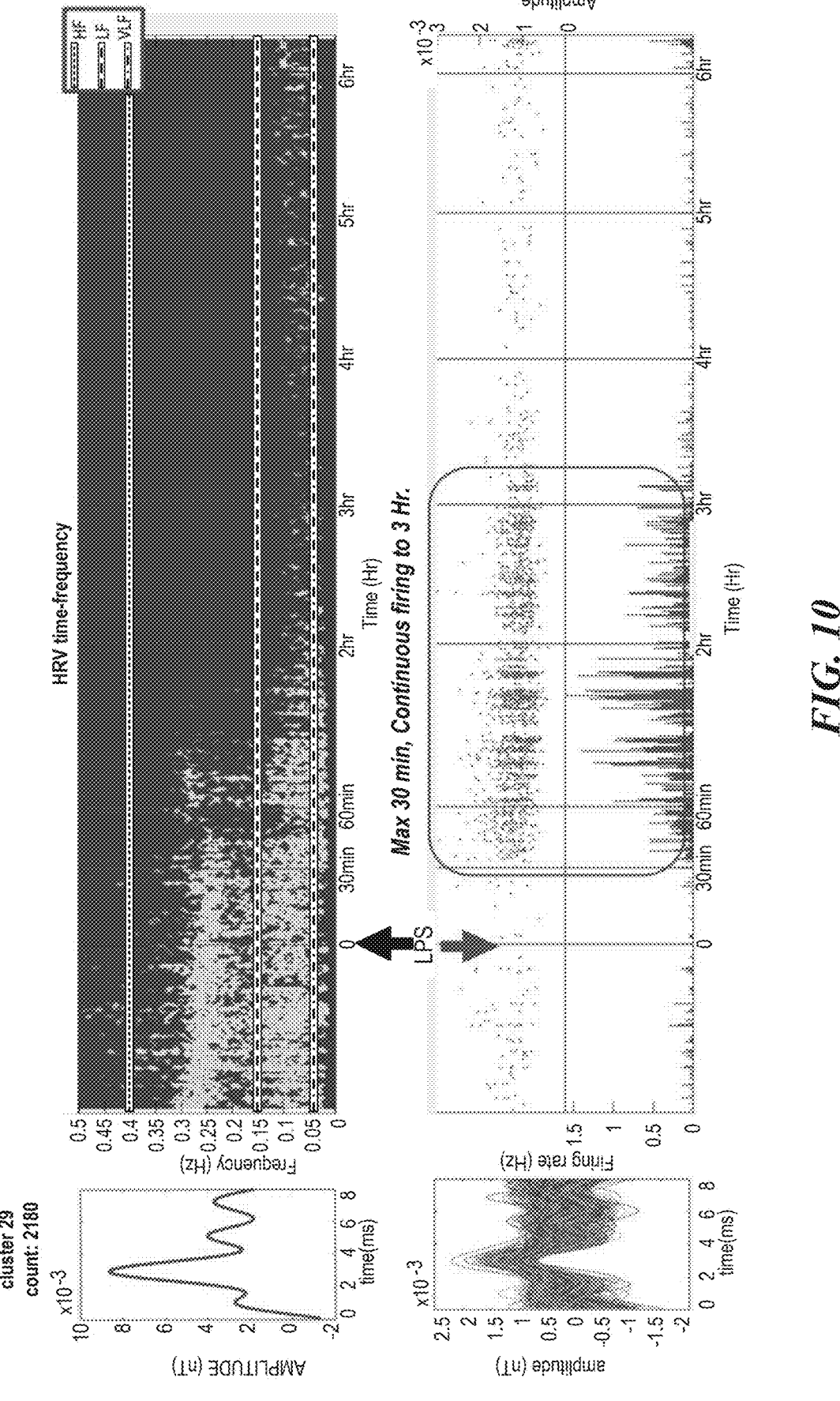
FIG. 10 is a data plot correlating a physiological signal to a neural signal from a second patient over a third duration in response to an LPS injection with a known bacterium.

FIG. 10 is a data plot correlating a physiological signal to a neural signal from a second patient over a third duration in response to an LPS injection with a known bacteria, consistent with disclosed embodiments. At least some of the data (e.g., 151, 251) presented in the data plot may have originated from a physiological signal. The physiological signal can include a heart rate signal of the second patient. The heart rate signal may have been communicated from a heart rate sensor. The data plot can present heart rate variability of the second patient. At least some of the data presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the second patient. The data plot may present a distinct firing pattern, a nested firing frequency, and/or a plurality of amplitudes for the one or more sensor signals. An immune response detector (e.g., 154, 254) can include instructions configured to cause a processing unit (e.g., 110, 210) to automatically detect an immune response based at least in part on the physiological signal and/or the one or more sensor signals.

Figure 11:
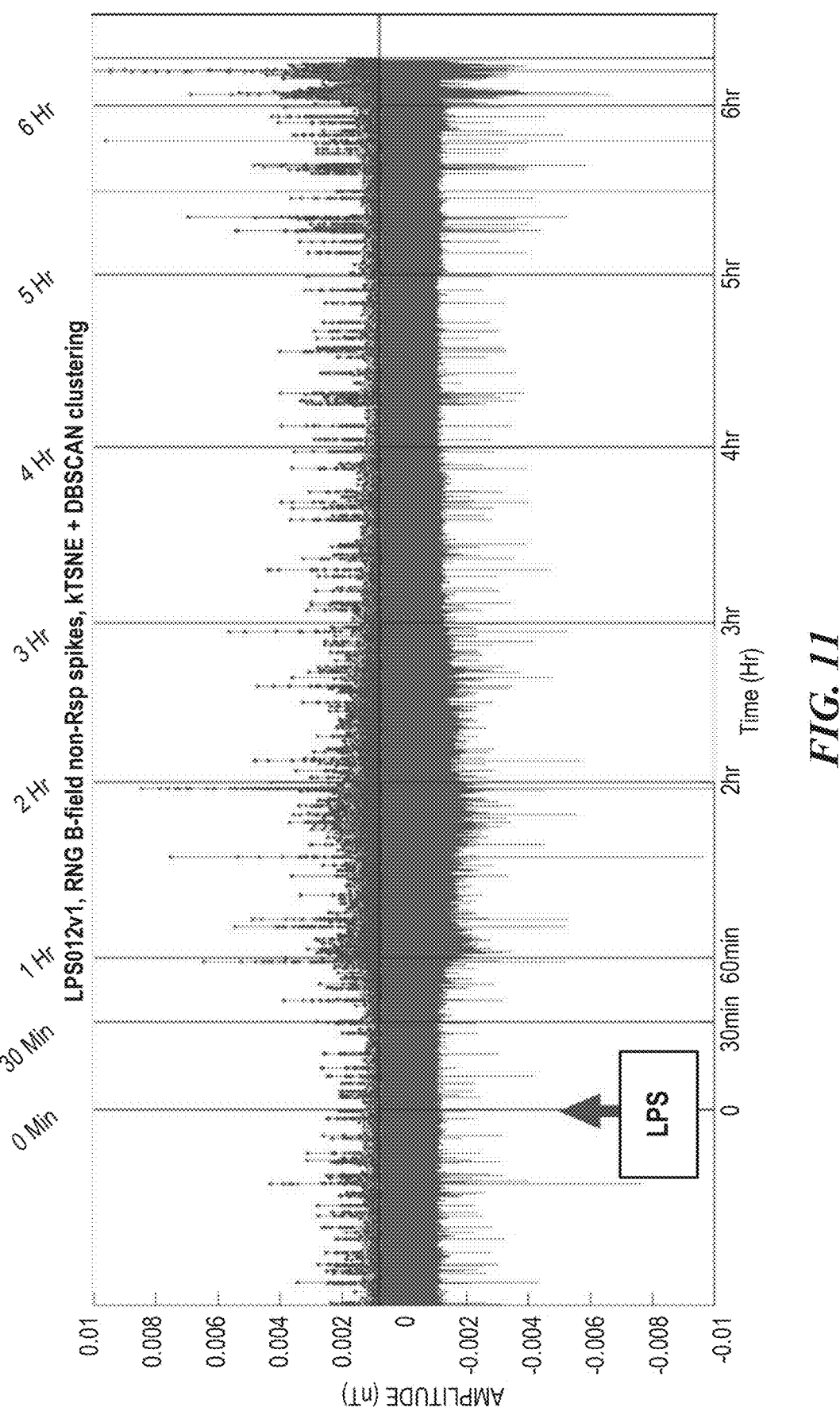
FIG. 11 is a data plot of a neural signal from a third patient in response to an LPS injection with a known bacterium.

FIG. 11 is a data plot of a neural signal from a third patient in response to an LPS injection with a known bacteria, consistent with disclosed embodiments. At least some of the data (e.g., 151, 251) presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the third patient. The data plot can present a distinct firing pattern, a nested firing frequency, and/or a plurality of amplitudes for the one or more sensor signals. An immune response detector (e.g., 154, 254) can include instructions configured to cause a processing unit (e.g., 110, 210) to automatically detect an immune response based at least in part on the one or more sensor signals.

Figure 12:
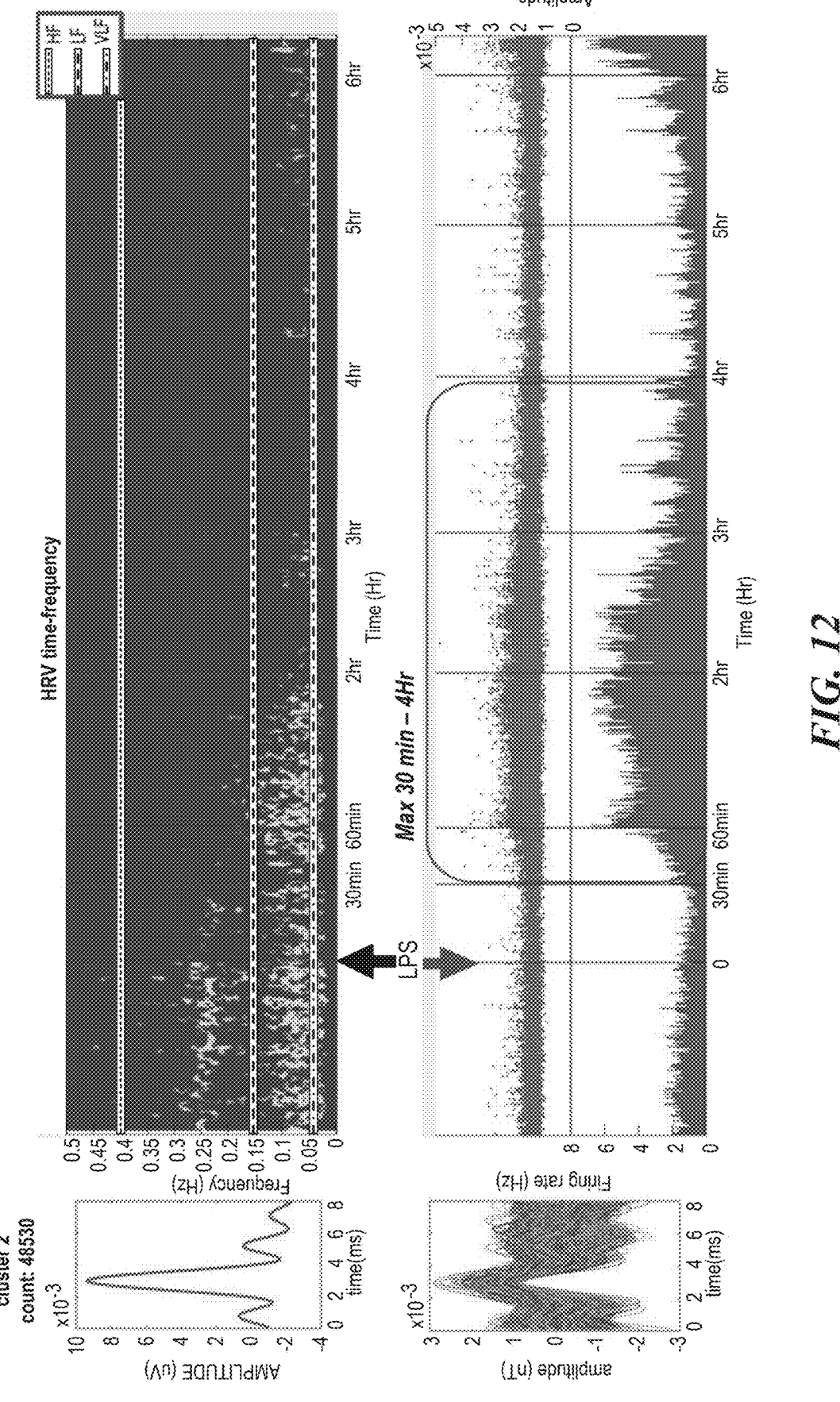
FIG. 12 is a data plot correlating a physiological signal to a neural signal from a third patient over a fourth duration in response to an LPS injection with a known bacterium.

FIG. 12 is a data plot correlating a physiological signal to a neural signal from a third patient over a fourth duration in response to an LPS injection with a known bacteria, consistent with disclosed embodiments. At least some of the data (e.g., 151, 251) presented in the data plot may have originated from a physiological signal. The physiological signal can include a heart rate signal of the third patient. The heart rate signal may have been communicated from a heart rate sensor. The data plot can present heart rate variability of the third patient. At least some of the data presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the third patient. The data plot can present a distinct firing pattern, a nested firing frequency, and/or a plurality of amplitudes for the one or more sensor signals. An immune response detector (e.g., 154, 254) can include instructions configured to cause a processing unit (e.g., 110, 210) to automatically detect an immune response based at least in part on the physiological signal and/or the one or more sensor signals.

As shown in FIG. 10 and FIG. 12, a duration in time in which an immune response to a known bacteria or other known stimuli is represented in neural signals and physiological signals may vary by subject, by stimuli, or by other conditions. For example, in FIG. 10, the third duration spans until three hours after the LPS injection of the known bacteria, whereas in FIG. 12, the fourth duration spans until four hours after the LPS injection of the known bacteria. In some embodiments, a historical label is generated to indicate a correlation between a duration of time and an immune response to a known stimulus.

Figure 13:
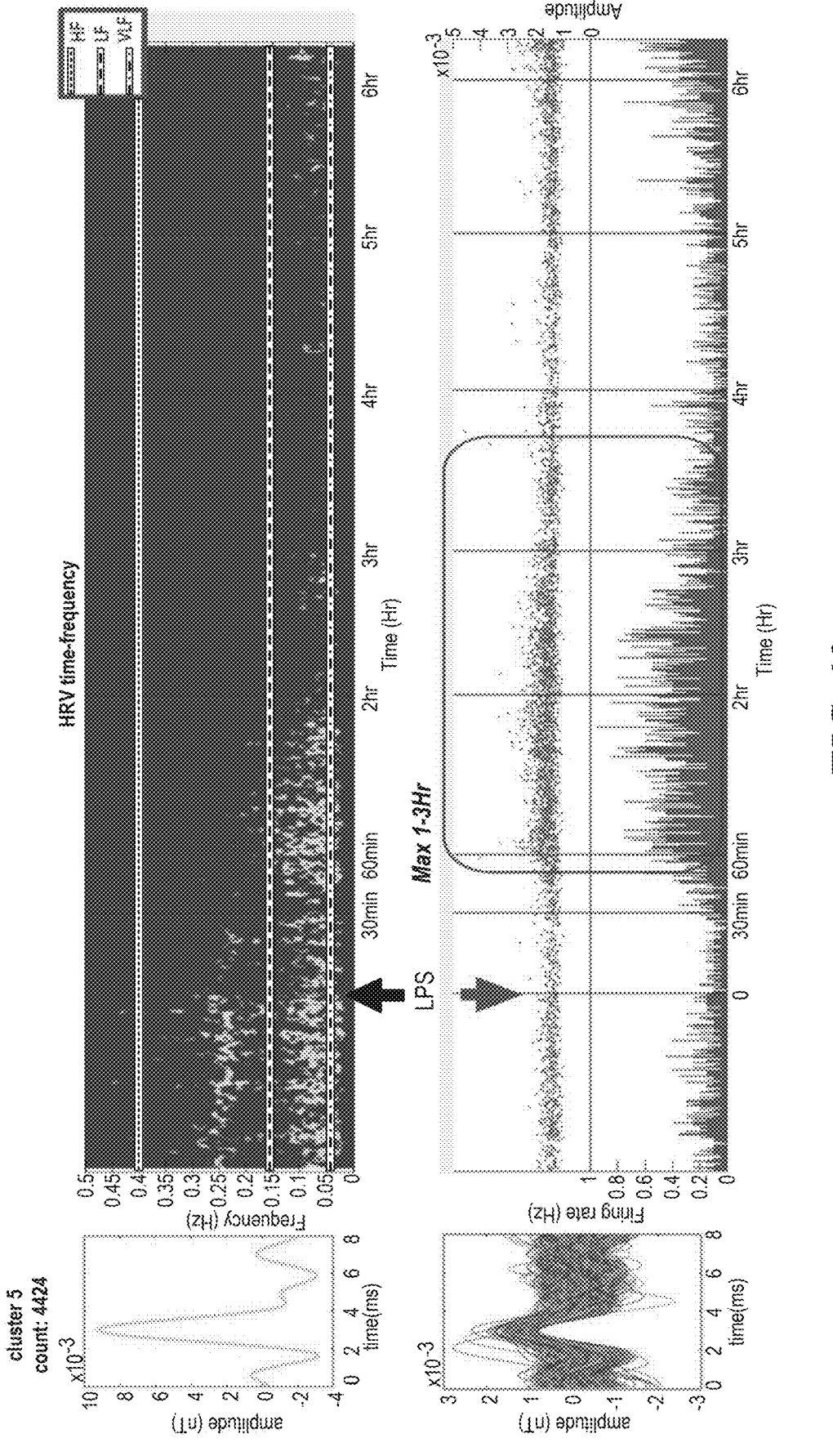
FIG. 13 is a data plot correlating a physiological signal to a neural signal from a third patient over a fifth duration in response to an LPS injection with a known bacterium.

FIG. 13 is a data plot correlating a physiological signal to a neural signal from a third patient over a fifth duration in response to an LPS injection with a known bacteria, consistent with disclosed embodiments. At least some of the data (e.g., 151, 251) presented in the data plot may have originated from a physiological signal. The physiological signal can include a heart rate signal of the third patient. The heart rate signal may have been communicated from a heart rate sensor. The data plot can present heart rate variability of the third patient. At least some of the data presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the third patient. The data plot may present a distinct firing pattern, a nested firing frequency, and/or a plurality of amplitudes for the one or more sensor signals. An immune response detector (e.g., 154, 254) can include instructions configured to cause a processing unit (e.g., 110, 210) to automatically detect an immune response based at least in part on the physiological signal and/or the one or more sensor signals.

Figure 14:
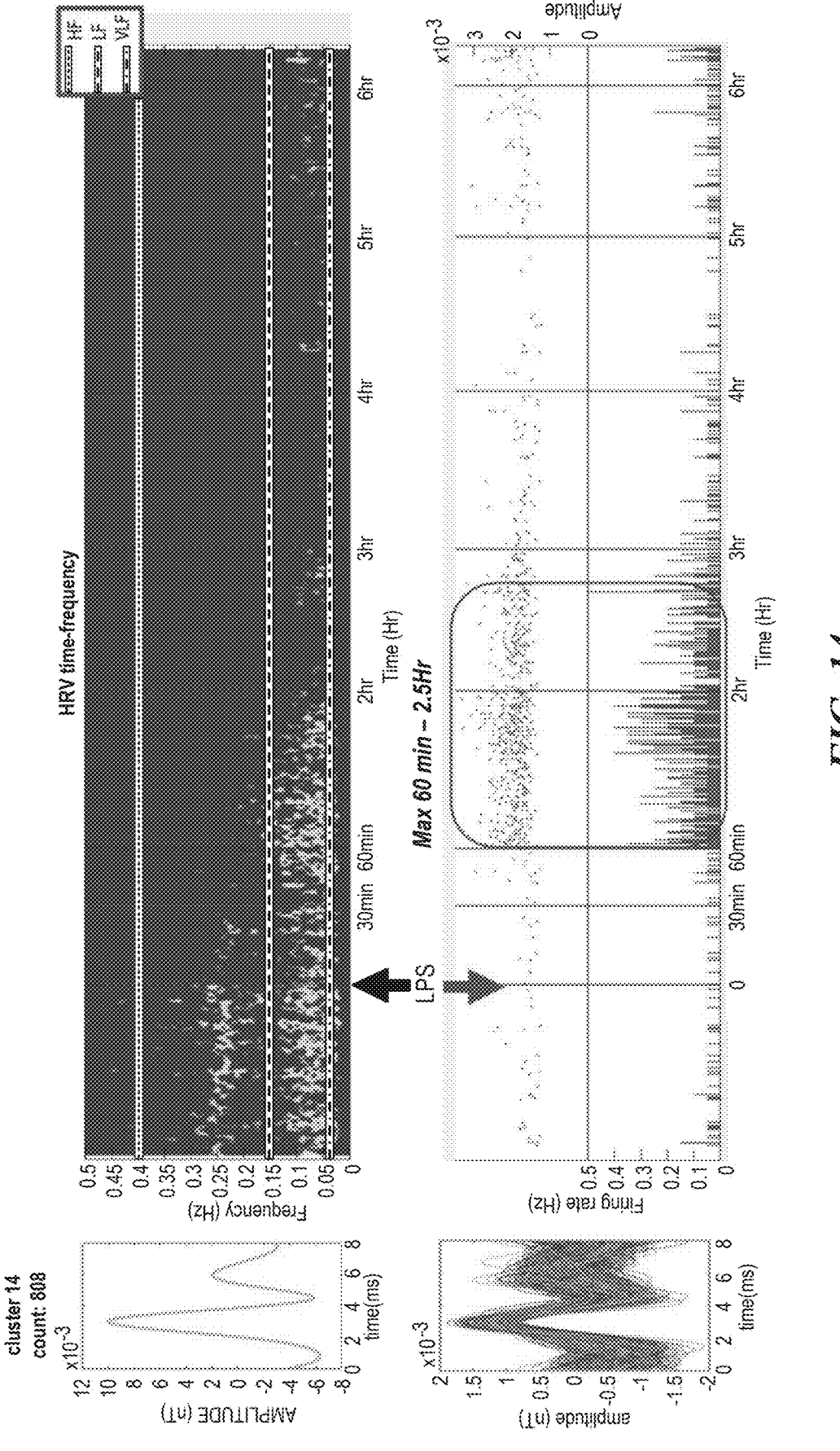
FIG. 14 is a data plot correlating a physiological signal to a neural signal from a third patient over a sixth duration in response to an LPS injection with a known bacterium.

FIG. 14 is a data plot correlating a physiological signal to a neural signal from a third patient over a sixth duration in response to an LPS injection with a known bacteria, consistent with disclosed embodiments. At least some of the data (e.g., 151, 251) presented in the data plot may have originated from a physiological signal. The physiological signal can include a heart rate signal of the third patient. The heart rate signal may have been communicated from a heart rate sensor. The data plot may present heart rate variability of the third patient. At least some of the data presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the third patient. The data plot can present a distinct firing pattern, a nested firing frequency, and/or a plurality of amplitudes for the one or more sensor signals. An immune response detector (e.g., 154, 254) can have instructions configured to cause a processing unit (e.g., 110, 210) to automatically detect an immune response based at least in part on the physiological signal and/or the one or more sensor signals.

Figure 15:
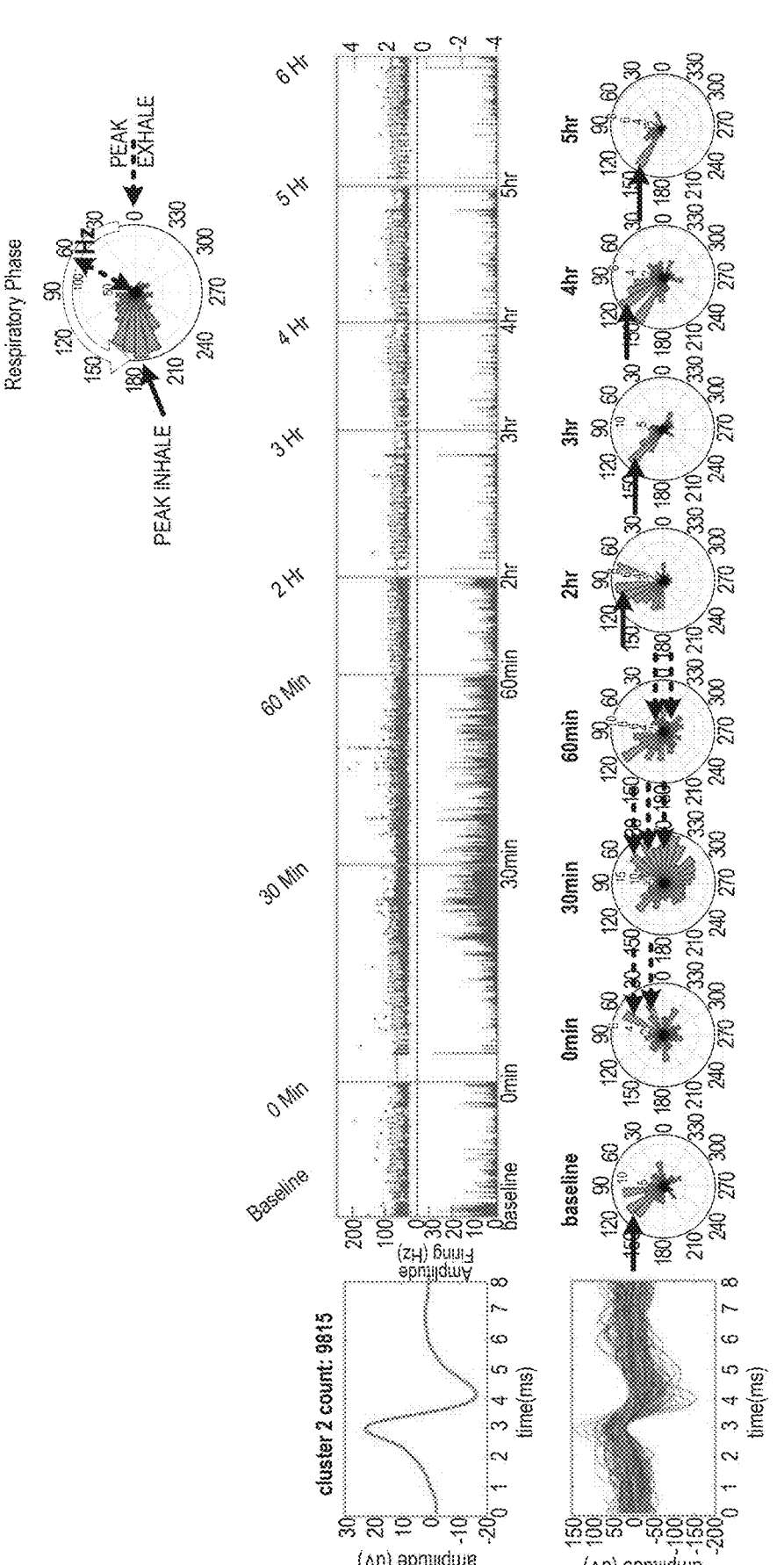
FIG. 15 is a data plot correlating a neural signal to a physiological signal from a second patient over a seventh duration in response to an LPS injection with a known bacterium.

FIG. 15 is a data plot correlating a neural signal to a physiological signal from a second patient over a seventh duration in response to an LPS injection with a known bacteria, consistent with disclosed embodiments. At least some of the data (e.g., 151, 251) presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the second patient. The data plot can present a distinct firing pattern, a nested firing frequency, and/or a plurality of amplitudes for the one or more sensor signals. At least some of the data presented in the data plot may have originated from a physiological signal. The physiological signal can have a respiratory signal. The respiratory signal may have been communicated from a respiration rate sensor. The data plot can present respiratory phase of the second patient. An immune response detector (e.g., 154, 254) may comprise instructions configured to cause a processing unit (e.g., 110, 210) to automatically detect an immune response based at least in part on the one or more sensor signals and/or the physiological signal.

Figure 16:
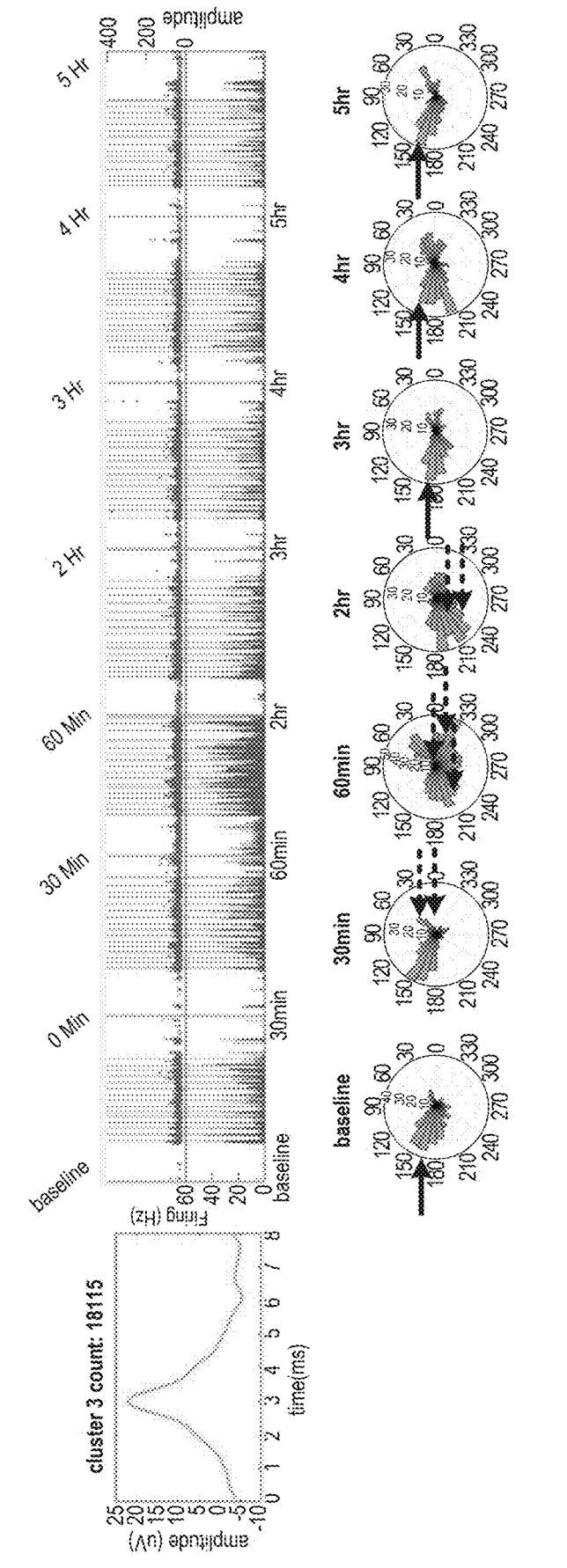
FIG. 16 is a data plot correlating a neural signal to a physiological signal from a fourth patient over a first duration in response to an LPS injection with a known bacterium.

FIG. 16 is a data plot correlating a neural signal to a physiological signal from a fourth patient over a first duration in response to an LPS injection with a known bacteria, consistent with disclosed embodiments. At least some of the data (e.g., 151, 251) presented in the data plot may have originated from one or more sensor signals (e.g., 135). The one or more sensor signals may have been communicated from one or more wearable sensors (e.g., 130) worn over a peripheral nerve (e.g., vagus nerve or sympathetic nerve) of the fourth patient. The data plot can present a distinct firing pattern, a nested firing frequency, and/or a plurality of amplitudes for the one or more sensor signals. At least some of the data presented in the data plot may have originated from a physiological signal. The physiological signal can have a respiratory signal. The respiratory signal may have been communicated from a respiration rate sensor. The data plot can present respiratory phase of the fourth patient. An immune response detector (e.g., 154, 254) can include instructions configured to cause a processing unit (e.g., 110, 210) to automatically detect an immune response based at least in part on the one or more sensor signals and/or the physiological signal.

Integrated Machine Learning Techniques for Non-Invasive Analysis of the Autonomic Nervous System for Early Detection of Immune Response Consistent with embodiments described herein, immune response detection and identification can be enhanced through using machine learning. Embodiments described herein provide non-invasive human immunotyping through machine learning using the autonomic nervous system.

The extreme diversity of the human immune system, forged and maintained throughout evolutionary history, provides a potent defense against pathogens. Immunity, however, is intrinsically variable because it is controlled by many polymorphic genes and is shaped by highly sensitive environmental sensors. Similarly, intrinsically variable autonomic neuro-immune regulation via-adrenergic receptor and α7-nicotinic acetylcholine receptor activity is controlled by polymorphic genes and environmental sensors.

Collectively, core functional configurations of autonomic regulation and immune response compose a host-to-pathogen response bias. While most healthy humans have the capacity to stimulate various types of immune cells, interferons, inflammasome activity, and vagal anti-inflammatory reflexes, individuals differ in the degree to which they are primed for each functional configuration.

Virulent emerging pathogens inherently circumvent these functional immune configurations and can impose a dysregulated hyperinflammatory response. Host-dependent baseline autonomic gradient drive (AGD) bias is detectible through high temporal resolution physiological monitoring and β-adrenergic receptor and α7-nicotinic acetylcholine receptor-mediated response characterization. Similar to immune bias, AGD bias was shown to predict current inflammatory status as well as severity of future inflammatory sequela and disease.

As described herein, lipopolysaccharide (LPS) is administered as an immune challenge to characterize subjects' individual and cohort differences between baseline and inflamed autonomic activity. By continuously monitoring various neural signals and physiological signals including cervical neuron firing, cardiac, and respiratory activities, a set of noninvasive features is developed for classification of high and low inflammation responders from baseline data.

FIG. 17 shows a diagram illustrating an example embodiment of a convolutional neural network (CNN) for an exemplary machine learning or deep learning model(s) in accordance with the present technology.

In some embodiments, a convolutional neural network (CNN) as shown in FIG. 17 or other exemplary machine learning or deep learning models are implemented to capture a 'snapshot' of a subject's basal autonomic activity and predict whether the subject will have a more adverse reaction to LPS administration. Although the immune response to LPS is performed in a controlled, replicable environment, this similar noninvasive method of analysis can be expanded in the clinical setting to obtain more robust patient data. In doing so, a patient's electronic health record (EHR) history can be leveraged to assist in classifying how an individual may respond to many different pathogens. By developing a predictive model of hybrid noninvasive autonomic and historical medical data features, positive patient outcomes can be increased through quantifying individual risk and providing clinical decision support.

Integrated Machine Learning Techniques for Non-Invasive Analysis of the Autonomic Nervous System for Early Detection of Sepsis Further example implementations of machine learning techniques in accordance with the present technology are described. Consistent with embodiment described herein related to immune response detection and identification, embodiments described herein leverage machine learning for noninvasive analysis of the human autonomic nervous system as a marker of early septicemia detection.

Sepsis, a dysregulated immune-mediated host response to infection, is one of the leading causes of morbidity and mortality among intensive care and post-operative care patients in the United States, causing roughly 1 out of 3 hospital deaths every year. Untreated sepsis may lead to septic shock, resulting in dilated and leaky blood vessels and severe hypotension and eventual damage to kidneys, lungs, and liver with mortality rates in excess of 40%. Indeed, each 1-hour delay in antibiotic administration after emergency department (ED) triage or onset of organ dysfunction may lead to a 3-7% increase in the probability of a poor outcome. This time-dependent intervention prescribes a need for identifying those at risk for sepsis and administering suitable treatment prior to observable clinical indications.

The current paradigm of infection diagnosis is informed by three things: the onset of clinical signs and symptoms of host response (e.g., fever, chills), the presence of signs of infection (e.g., dysuria, abnormal chest auscultation, purulent wounds), and a proven microbiological invasion of a sterile environment or signs of superinfection in a nonsterile environment (e.g., positive peritoneal tap, gastroenteritis). The onset of symptoms is largely a visual and behavioral cue for healthcare providers. The latter two sets of information then complement the visual diagnosis with clinical results and reports. More importantly, not all of this information may be present, or positive, in a patient. This paradigm necessitates the development of faster methods of infection detection that are patient-specific and that do not rely on visual markers.

Machine learning algorithms can be deployed in conjunction with embodiments described herein to detect septicemic risk earlier than healthcare providers and pre-symptomatically. As described herein, lipopolysaccharide (LPS) is intravenously administered to create a controlled, reproducible inflammatory response in humans. Various neural signals and physiological signals including heart rate, respiratory rate, and cervical neuron firing activity are continuously monitored as noninvasive measurements of autonomic nervous system (ANS) behavior. By measuring serum and symptom scores every hour, representative data of the ANS response to increasing cytokine levels is obtained.

FIG. 18 shows a diagram illustrating an example embodiment of a convolutional neural network (CNN) for an exemplary machine learning or deep learning model(s) in accordance with the present technology.

Utilizing a convolutional neural network (CNN) as shown in FIG. 18 or other exemplary machine learning or deep learning models to analyze the data sampled at various timescales, a point in time in which a patient is septicemic prior to symptom onset can be classified. Thus, this reflects that embodiments described herein relating to continuous noninvasive sensors of the ANS can be used to not only potentially detect the onset of sepsis in a hospital setting, but can provide clinical decision support as well.

Examples

In some example embodiments in accordance with the disclosed technology (example A1), a system includes a processing unit; a receiving unit configured to receive at least one sensor signal each communicated from a wearable sensor configured to detect at least one neural signal of a patient; and a tangible non-transitory computer readable medium comprising instructions configured to cause the processing unit to: automatically receive a data signal from the receiving unit; automatically detect an immune response based at least in part on the data signal; automatically create a notification based at least in part on the immune response; and automatically present the notification to a user of the system.

Example A2 includes the system according to any of examples A1-A18, wherein the processing unit is wearable.

Example A3 includes the system according to any of examples A1-A18, wherein the receiving unit is wearable.

Example A4 includes the system according to any of examples A1-A18, wherein the receiving unit is configured to detect the at least one neural signal in a vagus nerve or sympathetic nerve of the patient.

Example A5 includes the system according to any of examples A1-A18, wherein the receiving unit is configured to detect the at least one neural signal in a spinal nerve of the patient.

Example A6 includes the system according to any of examples A1-A18, wherein the computer readable medium is wearable.

Example A7 includes the system according to any of examples A1-A18, wherein the at least one sensor signal comprises at least one of: an electrocardiogram signal, an electroencephalographic signal, or a magnetization signal.

Example A8 includes the system according to any of examples A1-A18, wherein the at least one sensor signal comprises at least a portion of the neural signal.

Example A9 includes the system according to any of examples A1-A18, wherein the wearable sensor is configured to detect the at least one neural signal transcutaneously.

Example A10 includes the system according to any of examples A1-A18, wherein the receiving unit is further configured to differentiate between a plurality of neural signals.

Example A11 includes the system according to any of examples A1-A18, wherein the receiving unit is further configured to differentiate between a plurality of physiological signals.

Example A12 includes the system according to any of examples A1-A18, wherein the instructions are further configured to automatically determine that the immune response is based on an infection in the patient.

Example A13 includes the system according to any of examples A1-A18, wherein the instructions are further configured to automatically determine that the immune response is based on a cytokine response in the patient.

Example A14 includes the system according to any of examples A1-A18, wherein the instructions are further configured to automatically determine that the immune response is based on a specific pathogen in the patient.

Example A15 includes the system according to example A14 or any of examples A1-A18, wherein the specific pathogen is SARS-CoV-2.

Example A16 includes the system according to any of examples A1-A18, wherein the instructions are further configured to cause the processing unit to: automatically detect a change in the immune response; automatically create a change notification based at least in part on the change in the immune response; and automatically present the change notification to the user.

Example A17 includes the system according to any of examples A1-A18, wherein the instructions are further configured to cause the processing unit to automatically present a plot of the data signal on a display.

Example A18 includes the system according to any of examples A1-A17, further comprising at least one biofuel cell configured to power at least a portion of the system.

In some example embodiments in accordance with the disclosed technology (example A19), a method includes automatically receiving a sensor signal communicated from a wearable sensor configured to detect at least one neural signal of a patient; automatically detecting an immune response based at least in part on the sensor signal; automatically creating a notification based at least in part on the immune response; and automatically presenting the notification to a user.

Example A20 includes the method according to any of examples A19-A21, wherein the wearable sensor is configured to detect the at least one neural signal transcutaneously.

Example A21 includes the method according to any of examples A19-A20, further comprising automatically detecting a change in the immune response; automatically creating a change notification based at least in part on the change in the immune response; and automatically presenting the change notification to the user.

In some example embodiments in accordance with the disclosed technology (example A22), a system includes a processing unit; a receiving unit configured to receive at least one sensor signal each communicated from a wearable sensor configured to detect at least one neural signal of a patient; a transceiving unit configured to communicate with a remote device; and a tangible non-transitory computer readable medium comprising instructions configured to cause the processing unit to: automatically receive a data signal from the receiving unit; automatically detect an immune response based at least in part on the data signal; automatically create a notification based at least in part on the immune response; and automatically communicate the notification to the remote device employing the transceiving unit.

Example A23 includes the system according to any of examples A22-A40, wherein the processing unit is wearable.

Example A24 includes the system according to any of examples A22-A40, wherein the receiving unit is wearable.

Example A25 includes the system according to any of examples A22-A40, wherein the transceiving unit is wearable.

Example A26 includes the system according to any of examples A22-A40, wherein the receiving unit is configured to detect the at least one neural signal in a vagus nerve or sympathetic nerve of the patient.

Example A27 includes the system according to any of examples A22-A40, wherein the receiving unit is configured to detect the at least one neural signal in a spinal nerve of the patient.

Example A28 includes the system according to any of examples A22-A40, wherein the computer readable medium is wearable.

Example A29 includes the system according to any of examples A22-A40, wherein the at least one sensor signal comprises at least one of: an electrocardiogram signal, an electroencephalographic signal, or a magnetization signal.

Example A30 includes the system according to any of examples A22-A40, wherein the at least one sensor signal comprises at least a portion of the neural signal.

Example A31 includes the system according to any of examples A22-A40, wherein the wearable sensor is configured to detect the at least one neural signal transcutaneously.

Example A32 includes the system according to any of examples A22-A40, wherein the receiving unit is further configured to differentiate between a plurality of neural signals.

Example A33 includes the system according to any of examples A22-A40, wherein the receiving unit is further configured to differentiate between a plurality of physiological signals.

Example A34 includes the system according to any of examples A22-A40, wherein the instructions are further configured to automatically determine that the immune response is based on an infection in the patient.

Example A35 includes the system according to any of examples A22-A40, wherein the instructions are further configured to automatically determine that the immune response is based on a cytokine response in the patient.

Example A36 includes the system according to any of examples A22-A40, wherein the instructions are further configured to automatically determine that the immune response is based on a specific pathogen in the patient.

Example A37 includes the system according to example A36 or any of examples A22-A40, wherein the specific pathogen comprises SARS-CoV-2.

Example A38 includes the system according to any of examples A22-A40, wherein the instructions are further configured to cause the processing unit to: automatically detect a change in the immune response; automatically create a change notification based at least in part on the change in the immune response; and automatically communicate the change notification to the remote device employing the transceiving unit.

Example A39 includes the system according to any of examples A22-A40, wherein the instructions are further configured to cause the processing unit to automatically communicate the data signal to the remote device employing the transceiving unit.

Example A40 includes the system according to any of examples A22-A39, further comprising at least one biofuel cell configured to power at least a portion of the system.

In some example embodiments in accordance with the disclosed technology (example A41), a method includes automatically receiving a sensor signal communicated from a wearable sensor configured to detect at least one neural signal of a patient; automatically detecting an immune response based at least in part on the sensor signal; automatically creating a notification based at least in part on the immune response; and automatically communicating the notification to a remote device.

Example A42 includes the method according to any of examples A41-A43, wherein the wearable sensor is configured to detect the at least one neural signal transcutaneously.

Example A43 includes the method according to any of examples A41-A42, further comprising automatically detecting a change in the immune response; automatically creating a change notification based at least in part on the change in the immune response; and automatically communicating the change notification to the remote device.

In some example embodiments, in accordance with the disclosed technology (example B1), a method for early detection of immune response of a subject includes receiving, via a wearable sensor attached to a surface of the subject, at least one neural signal of the subject and at least one physiological signal of the subject detected by the wearable sensor; comparing a plurality of signal features across the at least one neural signal and the at least one physiological signal with historical signal labels associated with historical immune responses; based on the comparing, identifying an occurrence of an immune response of the subject; and causing a notification of the occurrence of the immune response to be presented to the subject via a personal device for the subject.

Example B2 includes the method of example B1, wherein the at least one neural signal includes a vagus nerve signal that is detected via an array of electrodes of the wearable sensor located at a cervical region of the subject.

Example B3 includes the method according to any of examples B1-B2, wherein the at least one neural signal includes a vagus nerve signal that is detected via an optically pumped magnetometer of the wearable sensor located at a cervical region of the subject.

Example B4 includes the method according to any of examples B1-B3, wherein identifying the occurrence of the immune response of the subject comprises classifying the immune response as one of: an inflammation, an infection, a cytokine response, a specific pathogen, or a specific disease.

Example B5 includes the method according to any of examples B1-B4, wherein the historical signal labels are associated with a resting state of the subject.

Example B6 includes the method according to any of examples B1-B5, wherein the plurality of signal features includes a cytokine-to-neural-signal value that is compared against a threshold in the historical signal labels.

Example B7 includes the method according to any of examples B1-B6, wherein the plurality of signal features includes a frequency of neural spike firings in the at least one neural signal.

Example B8 includes the method according to any of examples B1-B7, wherein the plurality of signal features across the at least one neural signal and the at least one physiological signal are identified based on correlating the at least one neural signal and the at least one physiological signal with respect to time.

Example B9 includes the method according to any of examples B1-B8, further including determining the historical signal labels associated with historical immune responses based on: obtaining a historical neural signal and a historical physiological signal over a duration of a historical immune response, and determining, via a data model, the historical signal labels to indicate a first correlation between features of the historical neural signal and the historical physiological signal and a second correlation between features of the historical neural signal and the historical immune response.

Example B10 includes the method according to Example B9, wherein the historical neural signal is obtained using an optically pumped magnetometer.

Example B11 includes a system for immune response identification that includes a wearable device attached to a surface of a subject, wherein the wearable device is configured to transcutaneously collect sensor data from the subject. The system further includes a processing unit comprising at least one processor and at least one memory, wherein the at least one processor executes instructions stored on the at least one memory to cause the processing unit to perform the method according to any of Examples B1-B10.

Example B12 includes a non-transitory computer readable medium having executable computer program code stored thereon. The executable computer program code includes instructions configured to cause a processor to perform the method according to any of Examples B1-B10.

In some example embodiments, in accordance with the disclosed technology (example C1), a system for pre-symptomatic detection of pathogen-stimulated immune responses via neural signals includes a processing unit including a processor that is configured to cause the system to, for a first subject stimulated with a known pathogen, obtain a neural signal and a physiological signal from a cervical region of the first subject through which a vagus nerve of the first subject extends. The neural signal includes a vagus nerve signal that is autonomically communicated through the vagus nerve as an immune response to the known pathogen. The processor is configured to further cause the system to extract, from the neural signal and the physiological signal, a plurality of historical labels that correlate signal features across the neural signal and the physiological signal with the known pathogen. The processor is configured to further cause the system to, for a second subject, monitor a second neural signal of the second subject via a wearable device adhered to a cervical region of the second subject through which a vagus nerve of the second subject extends. The processor is configured to further cause the system to, based on identifying a particular signal feature in the second neural signal that is correlated with the known pathogen according to the plurality of historical labels, determine an occurrence of the immune response to the known pathogen in the second subject. The processor is configured to further cause the system to cause a notification of the occurrence of the immune response to the known pathogen to be presented to the second subject via a personal device associated with the second subject.

In some example embodiments, in accordance with the disclosed embodiments (example D1), a system for pre-symptomatic detection of pathogen-stimulated immune responses via neural signals includes at least one processor and at least one memory, wherein the at least one processor executes instructions stored on the at least one memory to cause the system to: obtain, for a first subject stimulated with a known pathogen, a neural signal and a physiological signal from a cervical region of the first subject through which a vagus nerve of the first subject extends, wherein the neural signal includes a vagus nerve signal that is autonomically communicated through the vagus nerve as an immune response to the known pathogen; extract, from the neural signal and the physiological signal, a plurality of historical labels that correlate signal features across the neural signal and the physiological signal with the known pathogen; monitor, for a second subject, a second neural signal of the second subject via a wearable device adhered to a cervical region of the second subject through which a vagus nerve of the second subject extends; analyze the second neural signal to identify a particular signal feature in the second neural signal that is correlated with the known pathogen according to the plurality of historical labels; based on identifying the particular signal feature in the second neural signal, determine an occurrence of the immune response to the known pathogen in the second subject; and cause a notification of the occurrence of the immune response to the known pathogen to be presented to the second subject via a personal device associated with the second subject.

Example D2 includes the system of any of examples D1-D4, wherein the neural signal is obtained from the first subject for a duration of time subsequent to the first subject being stimulated with the known pathogen.

Example D3 includes the system of any of examples D1-D4, wherein the wearable device includes an optically pumped magnetometer (OPM) and/or an array of electrodes configured to detect the second neural signal.

Example D4 includes the system of any of examples D1-D3, wherein the second subject is the same as the first subject.

In some example embodiments, in accordance with the disclosed embodiments (example D5), a system for immune response identification includes a processing unit comprising at least one processor and at least one memory, wherein the at least one processor executes instructions stored on the at least one memory to cause the processing unit to: receive, via a wearable sensor device for a subject, at least one neural signal of the subject and at least one physiological signal of the subject detected by the wearable sensor device; compare a plurality of signal features across the at least one neural signal and the at least one physiological signal with historical signal labels associated with historical immune responses; based on the comparing, identify an occurrence of an immune response of the subject; and cause a notification of the occurrence of the immune response to be presented to the subject via a personal device for the subject.

Example D6 includes the system of any of examples D5-D15, further comprising the wearable sensor device, wherein the wearable sensor device is adherable to the cervical region of the subject and includes an OPM and/or an array of electrodes configured to transcutaneously collect sensor data from the subject.

Example D7 includes the system of example D6 or any of examples D5-D15, wherein the at least one neural signal includes a vagus nerve signal that is detected via an array of electrodes of the wearable sensor device located at a cervical region of the subject.

Example D8 includes the system of example D6 or any of examples D5-D15, wherein the at least one neural signal includes a vagus nerve signal that is detected via an optically pumped magnetometer of the wearable sensor device located at a cervical region of the subject.

Example D9 includes the system of any of examples D5-D15, wherein identifying the occurrence of the immune response of the subject comprises classifying the immune response as one of: an inflammation, an infection, a cytokine response, a specific pathogen, or a specific disease.

Example D10 includes the system of any of examples D5-D15, wherein the historical signal labels are associated with a resting state of the subject.

Example D11 includes the system of any of examples D5-D15, wherein the at least one processor executes instructions to further cause the processing unit to determine the historical signal labels associated with historical immune responses based on: obtaining a historical neural signal and a historical physiological signal over a duration of a historical immune response, and determining, via a data model, the historical signal labels to indicate a first correlation between features of the historical neural signal and the historical physiological signal and a second correlation between features of the historical neural signal and the historical immune response.

Example D12 includes the system of example D11 or any of examples D5-D15, wherein the historical neural signal is obtained using an optically pumped magnetometer (OPM).

Example D13 includes the system of any of examples D5-D15, wherein the plurality of signal features includes a cytokine-to-neural-signal value that is compared against a threshold in the historical signal labels.

Example D14 includes the system of any of examples D5-D15, wherein the plurality of signal features includes a frequency of neural spike firings in the at least one neural signal.

Example D15 includes the system of any of examples D5-D14, wherein the plurality of signal features across the at least one neural signal and the at least one physiological signal are identified based on correlating the at least one neural signal and the at least one physiological signal with respect to time.

In some example embodiments, in accordance with the disclosed embodiments (example D16), a non-transitory computer readable medium includes executable computer code stored thereon, where the executable computer code comprises instructions configured to cause a processor to perform operations comprising: receiving, via a wearable sensor attached to a surface of the subject, at least one neural signal of the subject and at least one physiological signal of the subject detected by the wearable sensor; comparing a plurality of signal features across the at least one neural signal and the at least one physiological signal with historical signal labels associated with one or more past immune responses; based on the comparing, identifying an occurrence of an immune response of the subject; and causing a notification of the occurrence of the immune response to be presented to the subject via a personal device for the subject.

Example D17 includes the non-transitory computer readable medium of any of examples D16-D25, wherein the at least one neural signal includes a vagus nerve signal that is detected via an array of electrodes of the wearable sensor located at a cervical region of the subject.

Example D18 includes the non-transitory computer readable medium of any of examples D16-D25, wherein the at least one neural signal includes a vagus nerve signal that is detected via an optically pumped magnetometer of the wearable sensor located at a cervical region of the subject.

Example D19 includes the non-transitory computer readable medium of any of examples D16-D25, wherein identifying whether the occurrence of the immune response of the subject comprises classifying the immune response as one of: an inflammation, an infection, a cytokine response, a specific pathogen, or a specific disease.

Example D20 includes the non-transitory computer readable medium of any of examples D16-D25, wherein the historical signal labels are associated with a resting state of the subject.

Example D21 includes the non-transitory computer readable medium of any of examples D16-D25, further comprising determining the historical signal labels associated with one or more past immune responses based on: obtaining a historical neural signal and a historical physiological signal over a duration of a past immune response, and determining, via a data model, the historical signal labels to indicate a first correlation between features of the historical neural signal and the historical physiological signal and a second correlation between features of the historical neural signal and the past immune response.

Example D22 includes the non-transitory computer readable medium of example D21 or any of examples D16-D25, wherein the historical neural signal is obtained using an optically pumped magnetometer (OPM).

Example D23 includes the non-transitory computer readable medium of any of examples D16-D25, wherein the plurality of signal features includes a cytokine-to-neural-signal value that is compared against a threshold in the historical signal labels.

Example D24 includes the non-transitory computer readable medium of any of examples D16-D25, wherein the plurality of signal features includes a frequency of neural spike firings in the at least one neural signal.

Example D25 includes the non-transitory computer readable medium of any of examples D16-D24, wherein the plurality of signal features across the at least one neural signal and the at least one physiological signal are identified based on correlating the at least one neural signal and the at least one physiological signal with respect to time.

In some example embodiments, in accordance with the disclosed embodiments (example D26), a system for neural signal detection of immune responses includes a processing unit comprising at least one processor and at least one memory; and a receiving unit comprising at least one receiver to receive sensor signals from a wearable sensor in communication with the receiving unit and to send data signals to the processing unit, the wearable sensor capable of detecting at least one signal associated with an immune response of a subject, wherein the at least one memory is coupled to the at least one processor and configured to store instructions that, when executed by the at least one processor, cause the system to perform operations comprising: receiving a data signal from the receiving unit, generating detection data associated with a detection of the immune response based at least in part on the data signal, producing a notification based at least in part on the detection data; and presenting the notification as an output.

Example D27 includes the system of any of examples D26-D28, wherein the output includes a plot of at least one data signal displayable on at least one display device.

Example D28 includes the system of any of examples D26-D27, wherein the at least one receiver includes a transceiving unit comprising a transmitter and a receiver configured to communicate with a remote device.

In some example embodiments, in accordance with the disclosed embodiments (example D29), a system for neural signal detection of immune responses includes a processing unit comprising at least one processor; a receiving unit comprising at least one receiver configured to receive sensor signals from a wearable sensor and send data signals to the processing unit, wherein the wearable sensor is configured to detect at least one signal; a sensor unit comprising one or more electric circuits configured to communicate with the receiving unit; and a tangible non-transitory computer readable medium comprising instructions configured to cause the processing unit to receive a data signal from the receiving unit, detect an immune response of a subject measured by the sensor unit based at least in part on the received data signal, generate a notification based at least in part on the detected immune response; and present the notification as an output.

Example D30 includes the system of any of examples D29-D33, wherein the one or more electric circuits are coupled to one or more sensors configured to detect a physiological signal transcutaneously.

Example D31 includes the system of any of examples D29-D33, wherein the system is operable to differentiate different signals having a waveform and an amplitude.

Example D32 includes the system of any of examples D29-D33, wherein the output includes a plot of at least one data signal displayable on at least one display device.

Example D33 includes the system of any of examples D29-D32, wherein the at least one receiver includes a transceiving unit comprising a transmitter and a receiver configured to communicate with a remote device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "a", "an", and "one" are not to be interpreted as "only one". In this specification, the phrase "based on" is indicative that the phrase following the term "based on" is an example of one of a multitude of suitable possibilities that may, or may not, be employed to one or more of the various embodiments. References to "an" embodiment in this disclosure are not necessarily to the same embodiment.

Many of the elements described in the disclosed embodiments may comprise computer instructions. At least a portion of the computer instructions may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element), or a combination thereof, all of which are behaviorally equivalent. For example, modules may be implemented using computer hardware in combination with software routine(s) written in a computer language (e.g., Java, HTML, XML, PHP, Python, ActionScript, JavaScript, Ruby, Prolog, SQL, VBScript, Visual Basic, Perl, C, C++, Objective-C, Rust, or the like). Additionally, it may be possible to implement modules using physical hardware that incorporates discrete or programmable analog, digital, and/or quantum hardware. Examples of programmable hardware include: computers, microcontrollers, microprocessors, application-specific integrated circuits (ASICs), field programmable gate arrays (FPGAs), and complex programmable logic devices (CPLDs). Computers, microcontrollers, and microprocessors are programmed using languages such as assembly, C, C++, or the like. FPGAs, ASICs, and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

Some embodiments may employ processing hardware. Processing hardware may include a processing unit, computer equipment, embedded systems, machines, and/or the like. The processing hardware may be configured to execute instructions. The instructions may be stored on a machine-readable medium. According to some embodiments, the machine-readable medium (e.g., automated data medium) may be a medium configured to store data in a machine-readable format that may be accessed by an automated sensing device. Examples of machine-readable media include flash memory, memory cards, electrically erasable programmable read-only memory (EEPROM), solid state drives, barcodes, magnetic ink characters, and/or the like.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes various embodiments have been described as communicating with at least one remote device. Persons skilled in the art will recognize that systems communicating with remote devices may vary from a traditional system/device relationship over a network such as the Internet. For example, a system may be collective based: portable equipment, broadcast equipment, virtual, application(s) distributed over a broad combination of computing sources, part of a cloud, combinations thereof, and/or the like. Similarly, for example, a remote device may be a user based client, portable equipment, broadcast equipment, virtual, application(s) distributed over a broad combination of computing sources, part of a cloud, combinations thereof, and/or the like. Additionally, it should be noted that, for example purposes, several of the various embodiments were described as comprising instructions. However, one skilled in the art will recognize that many various languages and frameworks may be employed to build and use embodiments of the present invention.

In this specification, various embodiments are disclosed. Limitations, features, and/or elements from the disclosed example embodiments may be combined to create further embodiments within the scope of the disclosure. Moreover, the scope includes any and all embodiments having equivalent elements, modifications, omissions, adaptations, or alterations based on the present disclosure. Further, aspects of the disclosed methods can be modified in any manner, including by reordering aspects, or inserting or deleting aspects.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Furthermore, many features presented above are described as being optional through the use of "may" or the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features, or with all three of the three possible features.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and attached appendix contain many specifics, these should not be construed as limitations on the scope of any invention or of what may be claimed, but rather as descriptions of features that may be specific to particular embodiments of particular inventions. Certain features that are described in this patent document and attached appendix in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendix should not be understood as requiring such separation in all embodiments.

Only a few implementations and examples are described and other implementations, enhancements and variations can be made based on what is described and illustrated in this patent document and attached appendix.

What is claimed is:

1. A system for immune response identification to detect a hyperinflammatory response, comprising:

a wearable sensor device configured to be worn against a cervical region of a subject, wherein the wearable sensor device comprises a magnetic field sensor and/or an array of electrodes configured to transcutaneously collect sensor data from the subject; and a processing unit comprising at least one processor and at least one memory, wherein the at least one processor executes instructions stored on the at least one memory to cause the processing unit to:

receive, via the wearable sensor device, a neural signal of the subject and a physiological signal of the subject detected by the wearable sensor device;

compare a plurality of signal features across the at least one neural signal and the at least one physiological signal with historical signal labels associated with historical immune responses from a database of historical signal labels specific to the patient and/or a demographic of the patient;

based on the comparing, identify an occurrence of an immune response of the subject indicating a hyper-inflammatory response; and cause a notification of the occurrence of the immune response to be presented.

2. The system of claim 1, wherein the magnetic field sensor includes an optically pumped magnetometer (OPM).

3. The system of claim 2, wherein the at least one neural signal includes a vagus nerve signal that is detected via an array of electrodes of the wearable sensor device located at the cervical region of the subject.

4. The system of claim 2, wherein the at least one neural signal includes a vagus nerve signal that is detected via an optically pumped magnetometer of the wearable sensor device located at the cervical region of the subject.

5. The system of claim 1, wherein identifying the occurrence of the immune response of the subject comprises classifying the immune response as one of: an inflammation, an infection, a cytokine response, a specific pathogen, or a specific disease.

6. The system of claim 1, wherein the historical signal labels are associated with a resting state of the subject.

7. The system of claim 1, wherein the at least one processor executes instructions to further cause the processing unit to determine the historical signal labels associated with historical immune responses based on: obtaining a historical neural signal and a historical physiological signal over a duration of a historical immune response, and determining, via a data model, the historical signal labels to indicate a first correlation between features of the historical neural signal and the historical physiological signal and a second correlation between features of the historical neural signal and the historical immune response.

8. The system of claim 7, wherein the historical neural signal is obtained using an optically pumped magnetometer (OPM) and/or an array of electrodes configured to transcutaneously collect sensor data from the subject.

9. The system of claim 1, wherein the plurality of signal features includes a cytokine-to-neural-signal value that is compared against a threshold in the historical signal labels.

10. The system of claim 1, wherein the plurality of signal features includes a frequency of neural spike firings in the at least one neural signal.

11. The system of claim 1, wherein the plurality of signal features across the at least one neural signal and the at least one physiological signal are identified based on correlating the at least one neural signal and the at least one physiological signal with respect to time.

12. A non-transitory computer readable medium having executable computer code stored thereon, the executable computer code comprising instructions configured to cause a processor to perform operations comprising:

receiving, via a wearable sensor attached to a surface of a subject, a neural signal of the subject and a physiological signal of the subject detected by the wearable sensor, wherein the neural signal comprises a vagus nerve signal that is detected by the wearable sensor from a cervical region of the subject;

comparing a plurality of signal features across the at least one neural signal and the at least one physiological signal with historical signal labels associated with one or more past immune responses from a database of historical signal labels specific to the patient and/or a demographic of the patient;

based on the comparing, identifying an occurrence of an immune response of the subject indicating sepsis; and causing a notification of the occurrence of the immune response to be presented.

13. The non-transitory computer readable medium of claim 12, wherein the at least one neural signal is detected via an array of electrodes of the wearable sensor.

14. The non-transitory computer readable medium of claim 12, wherein the at least one neural signal includes a vagus nerve signal that is detected via an optically pumped magnetometer of the wearable sensor located at a cervical region of the subject.

15. The non-transitory computer readable medium of claim 12, wherein identifying whether the occurrence of the immune response of the subject comprises classifying the immune response as one of: an inflammation, an infection, a cytokine response, a specific pathogen, or a specific disease.

16. The non-transitory computer readable medium of claim 12, wherein the historical signal labels are associated with a resting state of the subject.

17. The non-transitory computer readable medium of claim 12, further comprising determining the historical signal labels associated with one or more past immune responses based on: obtaining a historical neural signal and a historical physiological signal over a duration of a past immune response, and determining, via a data model, the historical signal labels to indicate a first correlation between features of the historical neural signal and the historical physiological signal and a second correlation between features of the historical neural signal and the past immune response.

18. The non-transitory computer readable medium of claim 17, wherein the historical neural signal is obtained using an optically pumped magnetometer (OPM).

19. The non-transitory computer readable medium of claim 12, wherein the plurality of signal features includes a cytokine-to-neural-signal value that is compared against a threshold in the historical signal labels.

20. The non-transitory computer readable medium of claim 12, wherein the plurality of signal features includes a frequency of neural spike firings in the at least one neural signal.

21. The non-transitory computer readable medium of claim 12, wherein the plurality of signal features across the at least one neural signal and the at least one physiological signal are identified based on correlating the at least one neural signal and the at least one physiological signal with respect to time.

* * * * *